`US009447441B2`

(12) United States Patent
Numata et al.

(10) Patent No.: US 9,447,441 B2
(45) Date of Patent: Sep. 20, 2016

(54) METHOD FOR PRODUCING POLYHYDROXYALKANOATE HAVING LONG MAIN CHAIN STRUCTURE

(75) Inventors: Keiji Numata, Saitama (JP); Miwa Yamada, Saitama (JP); Yoshiharu Doi, Saitama (JP)

(73) Assignee: RIKEN, Saitama (JP)

( * ) Notice: Subject to any disclaimer, the term of this patent is extended or adjusted under 35 U.S.C. 154(b) by 231 days.

(21) Appl. No.: 14/342,667

(22) PCT Filed: Apr. 13, 2012

(86) PCT No.: PCT/JP2012/060179
§ 371 (c)(1),
(2), (4) Date: Jun. 18, 2014

(87) PCT Pub. No.: WO2013/035372
PCT Pub. Date: Mar. 14, 2013

(65) Prior Publication Data
US 2014/0302572 A1   Oct. 9, 2014

(30) Foreign Application Priority Data

Sep. 5, 2011 (JP) .................... 2011-193230

(51) Int. Cl.
*C08G 63/06* (2006.01)
*C12P 7/62* (2006.01)

(52) U.S. Cl.
CPC .............. *C12P 7/625* (2013.01); *C08G 63/06* (2013.01)

(58) Field of Classification Search
CPC ................................ C08G 63/06; C12P 7/625
USPC ...................................................... 528/354
See application file for complete search history.

(56) References Cited

U.S. PATENT DOCUMENTS

| | | | |
|---|---|---|---|
| 6,316,262 B1 | 11/2001 | Huisman et al. | |
| 6,649,382 B1 | 11/2003 | Choi et al. | |
| 2010/0168481 A1 | 7/2010 | Farmer et al. | |

FOREIGN PATENT DOCUMENTS

| | | |
|---|---|---|
| EP | 0440165 | 8/1991 |
| JP | 2001-516574 | 10/2001 |
| JP | 2002-541759 | 12/2002 |
| WO | 99/14313 | 3/1999 |
| WO | 99/36547 | 7/1999 |
| WO | 2010/068953 | 6/2010 |

OTHER PUBLICATIONS

Steinbuchel et al., "Diversity of bacterial polyhydroxyalkanoic acids," *FEMS Microbiology Letters*, vol. 128, pp. 219-228, 1995.
Taguchi et al., "A microbial factory for lactate-based polyesters using a lactate-polymerizing enzyme," *Proc. Natl. Acad. Sci.*, vol. 105, pp. 17323-17327, 2008.
Kunioka et al., "New bacterial copolyesters produced in *Alcaligenes eutrophus* from organic acids," *Polymer Communications*, vol. 29, pp. 174-176, 1988.
Gorenflo et al., "Development of a Process for a Biotechnological Large-Scale Production of 4-Hydroxyvalerate-Containing Polyesters and Characterization of Their Physical and Mechanical Properties," *Biomacromolecules*, vol. 2, pp. 45-57, 2001.
Doi et al., "Biosynthesis of terpolyesters of 3-hydroxybutyrate, 3-hydroxyvalerate, and 5-hydroxyvalerate in *Alcaligenes eutrophus* from 5-chloropentanoic and pentanoic acids," *Makromol Chem., Rapid Commun.*, vol. 8, pp. 631-635, 1987.
Choi et al., "Biosynthesis and Local Sequence Specific Degradation of Poly(3-hydroxyvalerate-*co*-4-hydroxybutyrate) in *Hydrogenophaga pseudoflava*," *Biomacromolecules*, vol. 4, pp. 38-45, 2003.
Nomura et al., "PHA synthase engineering toward superbiocatalysts for custom-made biopolymers" *Appl. Microbiol. Biotechnol.*, vol. 73, pp. 969-979, 2007.
Taguchi et al., "Evolution of Polyhydroxyalkanoate (PHA) Production System by 'Enzyme Evolution': Successful Case Studies of Directed Evolution," *Macromol. Biosci.*, vol. 4, pp. 145-156, 2004.
Taguchi et al., "Biosynthesis of biodegradable polyesters from renewable carbon sources by recombinant bacteria," *Polymer International*, vol. 51, pp. 899-906, 2002.
Yamada et al., "Microbial Production of Bioplastic Polyhydroxyalkanoate with Long Main-Chain Monomer Units" from *A Summary of the 2011 Annual Meeting of the Japan Society for Bioscience, Biotechnology and Agrochemistry*, published Mar. 5, 2011, p. 3 (2C01p07).
Yamada et al., "Choshusa Monomer Unit o Yusuru Polyhydroxyalkanoate no Biseibutsu Gosei," *Polymer Preprints*, vol. 60, No. 2, pp. 5245-5246, Japan, Sep. 13, 2011.
International Search Report for PCT/JP2012/060179, mailed Jul. 17, 2012.
Japanese Office Action issued with respect to application No. 2013-532472, mail date is Jan. 19, 2016.
K. Numata et al., "Studies regarding Bioplastics Production Using Marine Microorganism Vibrio sp. and Related Genes Thereof", Japanese Society for Marine Biotechnology, 2A-11, 2011.
European Search Report in related application No. 12829695.1, mail date Mar. 19, 2015.

*Primary Examiner* — Ling Choi
*Assistant Examiner* — Gennadiy Mesh
(74) *Attorney, Agent, or Firm* — Greenblum and Bernstein, P.L.C

(57) ABSTRACT

A polyhydroxyalkanoate copolymer of 3HB (3-hydroxybutyrate), 3HP (3-hydroxypropionate) and 5HV (5-hydroxyvalerate) disclosed. The polyhydroxyalkanoate can be used for bioplastic or biomaterial. A method for producing the polyhydroxyalkanoate comprises culturing a microorganism belonging to *Ralstonia* genus in a culture medium that comprises lactone and/or hydroxy acid or salt of hydroxy acid as a carbon source.

4 Claims, 5 Drawing Sheets

(A)

(B)

SEQUENCE LISTING

<160> NUMBER OF SEQ ID NOS: 6

<210> SEQ ID NO 1
<211> LENGTH: 1767
<212> TYPE: DNA
<213> ORGANISM: Ralstonia eutropha
<220> FEATURE:
<221> NAME/KEY: CDS
<222> LOCATION: (1)..(1764)

<400> SEQUENCE: 1

```
atg gcg acc ggc aaa ggc gcg gca gct tcc acg cag gaa ggc aag tcc        48
Met Ala Thr Gly Lys Gly Ala Ala Ala Ser Thr Gln Glu Gly Lys Ser
1               5                   10                  15 caa cca ttc aag gtc acg ccg ggg cca ttc gat cca gcc aca tgg ctg        96
Gln Pro Phe Lys Val Thr Pro Gly Pro Phe Asp Pro Ala Thr Trp Leu
                20                  25                  30 gaa tgg tcc cgc cag tgg cag ggc act gaa ggc aac ggc cac gcg gcc       144
Glu Trp Ser Arg Gln Trp Gln Gly Thr Glu Gly Asn Gly His Ala Ala
            35                  40                  45 gcg tcc ggc att ccg ggc ctg gat gcg ctg gca ggc gtc aag atc gcg       192
Ala Ser Gly Ile Pro Gly Leu Asp Ala Leu Ala Gly Val Lys Ile Ala
        50                  55                  60 ccg gcg cag ctg ggt gat atc cag cag cgc tac atg aag gac ttc tca       240
Pro Ala Gln Leu Gly Asp Ile Gln Gln Arg Tyr Met Lys Asp Phe Ser
65                  70                  75                  80 gcg ctg tgg cag gcc atg gcc gag ggc aag gcc gag gcc acc ggt ccg       288
Ala Leu Trp Gln Ala Met Ala Glu Gly Lys Ala Glu Ala Thr Gly Pro
                85                  90                  95 ctg cac gac cgg cgc ttc gcc ggc gac gca tgg cgc acc aac ctc cca       336
Leu His Asp Arg Arg Phe Ala Gly Asp Ala Trp Arg Thr Asn Leu Pro
                100                 105                 110 tat cgc ttc gct gcc gcg ttc tac ctg ctc aat gcg cgc gcc ttg acc       384
Tyr Arg Phe Ala Ala Ala Phe Tyr Leu Leu Asn Ala Arg Ala Leu Thr
            115                 120                 125 gag ctg gcc gat gcc gtc gag gcc gat gcc aag acc cgc cag cgc atc       432
Glu Leu Ala Asp Ala Val Glu Ala Asp Ala Lys Thr Arg Gln Arg Ile
        130                 135                 140 cgc ttc gcg atc tcg caa tgg gtc gat gcg atg tcg ccc gcc aac ttc       480
Arg Phe Ala Ile Ser Gln Trp Val Asp Ala Met Ser Pro Ala Asn Phe
145                 150                 155                 160 ctt gcc acc aat ccc gag gcg cag cgc ctg ctg atc gag tcg ggc ggc       528
Leu Ala Thr Asn Pro Glu Ala Gln Arg Leu Leu Ile Glu Ser Gly Gly
                165                 170                 175 gaa tcg ctg cgt gcc ggc gtg cgc aac atg atg gaa gac ctg aca cgc       576
Glu Ser Leu Arg Ala Gly Val Arg Asn Met Met Glu Asp Leu Thr Arg
                180                 185                 190
```

-continued

| | | |
|---|---|---|
| ggc aag atc tcg cag acc gac gag agc gcg ttt gag gtc ggc cgc aat<br>Gly Lys Ile Ser Gln Thr Asp Glu Ser Ala Phe Glu Val Gly Arg Asn<br>     195                         200                       205 | | 624 |
| gtc gcg gtg acc gaa ggc gcc gtg gtc ttc gag aac gag tac ttc cag<br>Val Ala Val Thr Glu Gly Ala Val Val Phe Glu Asn Glu Tyr Phe Gln<br>210                       215                      220 | | 672 |
| ctg ttg cag tac aag ccg ttg acc gac aag gtg cac gcg cgc ccg ctg<br>Leu Leu Gln Tyr Lys Pro Leu Thr Asp Lys Val His Ala Arg Pro Leu<br>225                       230                    235                240 | | 720 |
| ctg atg gtg ccg ccg tgc atc aac aag tac tac atc ctg gac ctg cag<br>Leu Met Val Pro Pro Cys Ile Asn Lys Tyr Tyr Ile Leu Asp Leu Gln<br>                   245                    250                    255 | | 768 |
| ccg gag agc tcg ctg gtg cgc cat gtg gtg gag cag gga cat acg gtg<br>Pro Glu Ser Ser Leu Val Arg His Val Val Glu Gln Gly His Thr Val<br>               260                    265                    270 | | 816 |
| ttt ctg gtg tcg tgg cgc aat ccg gac gcc agc atg gcc ggc agc acc<br>Phe Leu Val Ser Trp Arg Asn Pro Asp Ala Ser Met Ala Gly Ser Thr<br>     275                     280                    285 | | 864 |
| tgg gac gac tac atc gag cac gcg gcc atc cgc gcc atc gaa gtc gcg<br>Trp Asp Asp Tyr Ile Glu His Ala Ala Ile Arg Ala Ile Glu Val Ala<br>290                       295                    300 | | 912 |
| cgc gac atc agc ggc cag gac aag atc aac gtg ctc ggc ttc tgc gtg<br>Arg Asp Ile Ser Gly Gln Asp Lys Ile Asn Val Leu Gly Phe Cys Val<br>305                       310                    315                320 | | 960 |
| ggc ggc acc att gtc tcg acc gcg ctg gcg gtg ctg gcc gcg cgc ggc<br>Gly Gly Thr Ile Val Ser Thr Ala Leu Ala Val Leu Ala Ala Arg Gly<br>               325                    330                    335 | | 1008 |
| gag cac ccg gcc gcc agc gtc acg ctg ctg acc acg ctg ctg gac ttt<br>Glu His Pro Ala Ala Ser Val Thr Leu Leu Thr Thr Leu Leu Asp Phe<br>               340                    345                    350 | | 1056 |
| gcc gac acg ggc atc ctc gac gtc ttt gtc gac gag ggc cat gtg cag<br>Ala Asp Thr Gly Ile Leu Asp Val Phe Val Asp Glu Gly His Val Gln<br>               355                    360                    365 | | 1104 |
| ttg cgc gag gcc acg ctg ggc ggc ggc gcc ggc gcg ccg tgc gcg ctg<br>Leu Arg Glu Ala Thr Leu Gly Gly Gly Ala Gly Ala Pro Cys Ala Leu<br>     370                     375                    380 | | 1152 |
| ctg cgc ggc ctt gag ctg gcc aat acc ttc tcg ttc ttg cgc ccg aac<br>Leu Arg Gly Leu Glu Leu Ala Asn Thr Phe Ser Phe Leu Arg Pro Asn<br>385                       390                    395                400 | | 1200 |
| gac ctg gtg tgg aac tac gtg gtc gac aac tac ctg aag ggc aac acg<br>Asp Leu Val Trp Asn Tyr Val Val Asp Asn Tyr Leu Lys Gly Asn Thr<br>                   405                    410                    415 | | 1248 |
| ccg gtg ccg ttc gac ctg ctg ttc tgg aac ggc gac gcc acc aac ctg<br>Pro Val Pro Phe Asp Leu Leu Phe Trp Asn Gly Asp Ala Thr Asn Leu<br>               420                    425                    430 | | 1296 |
| ccg ggg ccg tgg tac tgc tgg tac ctg cgc cac acc tac ctg cag aac<br>Pro Gly Pro Trp Tyr Cys Trp Tyr Leu Arg His Thr Tyr Leu Gln Asn<br>           435                     440                    445 | | 1344 |
| gag ctc aag gta ccg ggc aag ctg acc gtg tgc ggc gtg ccg gtg gac<br>Glu Leu Lys Val Pro Gly Lys Leu Thr Val Cys Gly Val Pro Val Asp<br>450                       455                    460 | | 1392 |
| ctg gcc agc atc gac gtg ccg acc tat atc tac ggc tcg cgc gaa gac<br>Leu Ala Ser Ile Asp Val Pro Thr Tyr Ile Tyr Gly Ser Arg Glu Asp<br>465                       470                    475                480 | | 1440 |
| cat atc gtg ccg tgg acc gcg gcc tat gcc tcg acc gcg ctg ctg gcg<br>His Ile Val Pro Trp Thr Ala Ala Tyr Ala Ser Thr Ala Leu Leu Ala<br>                   485                    490                    495 | | 1488 |
| aac aag ctg cgc ttc gtg ctg ggt gcg tcg ggc cat atc gcc ggt gtg<br>Asn Lys Leu Arg Phe Val Leu Gly Ala Ser Gly His Ile Ala Gly Val | | 1536 |

```
                500                    505                    510
atc aac ccg ccg gcc aag aac aag cgc agc cac tgg act aac gat gcg      1584
Ile Asn Pro Pro Ala Lys Asn Lys Arg Ser His Trp Thr Asn Asp Ala
        515                    520                    525 ctg ccg gag tcg ccg cag caa tgg ctg gcc ggc gcc atc gag cat cac      1632
Leu Pro Glu Ser Pro Gln Gln Trp Leu Ala Gly Ala Ile Glu His His
530                    535                    540 ggc agc tgg tgg ccg gac tgg acc gca tgg ctg gcc ggg cag gcg gcg      1680
Gly Ser Trp Trp Pro Asp Trp Thr Ala Trp Leu Ala Gly Gln Ala Ala
545                    550                    555                    560 cga aac gcg ccg cgc ccg cca act atg gca atg cgc tat cgc gca atc      1728
Arg Asn Ala Pro Arg Pro Pro Thr Met Ala Met Arg Tyr Arg Ala Ile
                565                    570                    575 gaa ccc gcg cct ggg cga tac gtc aaa gcc aag gca tga                  1767
Glu Pro Ala Pro Gly Arg Tyr Val Lys Ala Lys Ala
                580                    585

<210> SEQ ID NO 2
<211> LENGTH: 588
<212> TYPE: PRT
<213> ORGANISM: Ralstonia eutropha

<400> SEQUENCE: 2

Met Ala Thr Gly Lys Gly Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
```

```
                    260                 265                 270
Phe Leu Val Ser Trp Arg Asn Pro Asp Ala Ser Met Ala Gly Ser Thr
                275                 280                 285

Trp Asp Asp Tyr Ile Glu His Ala Ala Ile Arg Ala Ile Glu Val Ala
            290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
            355                 360                 365

Leu Arg Glu Ala Thr Leu Gly Gly Ala Gly Ala Pro Cys Ala Leu
            370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
            435                 440                 445

Glu Leu Lys Val Pro Gly Lys Leu Thr Val Cys Gly Val Pro Val Asp
450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
            515                 520                 525

Leu Pro Glu Ser Pro Gln Gln Trp Leu Ala Gly Ala Ile Glu His His
            530                 535                 540

Gly Ser Trp Trp Pro Asp Trp Thr Ala Trp Leu Ala Gly Gln Ala Ala
545                 550                 555                 560

Arg Asn Ala Pro Arg Pro Pro Thr Met Ala Met Arg Tyr Arg Ala Ile
                565                 570                 575

Glu Pro Ala Pro Gly Arg Tyr Val Lys Ala Lys Ala
            580                 585

<210> SEQ ID NO 3
<211> LENGTH: 1680
<212> TYPE: DNA
<213> ORGANISM: Pseudomonas sp.
<220> FEATURE:
<223> OTHER INFORMATION: 61-3
<220> FEATURE:
<221> NAME/KEY: CDS
<222> LOCATION: (1)..(1677)

<400> SEQUENCE: 3 atg agt aac aag aat agc gat gac ttg aat cgt caa gcc tcg gaa aac      48
Met Ser Asn Lys Asn Ser Asp Asp Leu Asn Arg Gln Ala Ser Glu Asn
1               5                   10                  15
```

| | | | | | | | | | | | | | | | | |
|---|---|---|---|---|---|---|---|---|---|---|---|---|---|---|---|---|
| acc | ttg | ggg | ctt | aac | cct | gtc | atc | ggc | ctg | cgt | gga | aaa | gat | ctg | ctg | 96 |
| Thr | Leu | Gly | Leu | Asn | Pro | Val | Ile | Gly | Leu | Arg | Gly | Lys | Asp | Leu | Leu | |
| | | | 20 | | | | 25 | | | | | 30 | | | | |

| | | | | | | | | | | | | | | | | |
|---|---|---|---|---|---|---|---|---|---|---|---|---|---|---|---|---|
| act | tct | gcc | cga | atg | gtt | tta | acc | caa | gcc | atc | aaa | caa | ccc | att | cac | 144 |
| Thr | Ser | Ala | Arg | Met | Val | Leu | Thr | Gln | Ala | Ile | Lys | Gln | Pro | Ile | His | |
| | | 35 | | | | 40 | | | | 45 | | | | | | |

| | | | | | | | | | | | | | | | | |
|---|---|---|---|---|---|---|---|---|---|---|---|---|---|---|---|---|
| agc | gtc | aag | cac | gtc | gcg | cat | ttt | ggc | atc | gag | ctg | aag | aac | gtg | atg | 192 |
| Ser | Val | Lys | His | Val | Ala | His | Phe | Gly | Ile | Glu | Leu | Lys | Asn | Val | Met | |
| | 50 | | | | 55 | | | | 60 | | | | | | | |

| | | | | | | | | | | | | | | | | |
|---|---|---|---|---|---|---|---|---|---|---|---|---|---|---|---|---|
| ttt | ggc | aaa | tcg | aag | ctg | caa | ccg | gaa | agc | gat | gac | cgt | cgt | ttc | aac | 240 |
| Phe | Gly | Lys | Ser | Lys | Leu | Gln | Pro | Glu | Ser | Asp | Asp | Arg | Arg | Phe | Asn | |
| 65 | | | | 70 | | | | 75 | | | | 80 | | | | |

| | | | | | | | | | | | | | | | | |
|---|---|---|---|---|---|---|---|---|---|---|---|---|---|---|---|---|
| gac | ccc | gcc | tgg | agt | cag | aac | cca | ctc | tac | aaa | cgt | tat | cta | caa | acc | 288 |
| Asp | Pro | Ala | Trp | Ser | Gln | Asn | Pro | Leu | Tyr | Lys | Arg | Tyr | Leu | Gln | Thr | |
| | | | | 85 | | | | 90 | | | | 95 | | | | |

| | | | | | | | | | | | | | | | | |
|---|---|---|---|---|---|---|---|---|---|---|---|---|---|---|---|---|
| tac | ctg | gcg | tgg | cgc | aag | gaa | ctc | cac | gac | tgg | atc | ggc | aac | agc | aaa | 336 |
| Tyr | Leu | Ala | Trp | Arg | Lys | Glu | Leu | His | Asp | Trp | Ile | Gly | Asn | Ser | Lys | |
| | | | 100 | | | | 105 | | | | 110 | | | | | |

| | | | | | | | | | | | | | | | | |
|---|---|---|---|---|---|---|---|---|---|---|---|---|---|---|---|---|
| ctg | tcc | gaa | cag | gac | atc | aat | cgc | gct | cac | ttc | gtg | atc | acc | ctg | atg | 384 |
| Leu | Ser | Glu | Gln | Asp | Ile | Asn | Arg | Ala | His | Phe | Val | Ile | Thr | Leu | Met | |
| | | | 115 | | | | 120 | | | | 125 | | | | | |

| | | | | | | | | | | | | | | | | |
|---|---|---|---|---|---|---|---|---|---|---|---|---|---|---|---|---|
| acc | gaa | gcc | atg | gcc | ccg | acc | aac | agt | gcg | gcc | aat | ccg | gcg | gcg | gtc | 432 |
| Thr | Glu | Ala | Met | Ala | Pro | Thr | Asn | Ser | Ala | Ala | Asn | Pro | Ala | Ala | Val | |
| | 130 | | | | 135 | | | | 140 | | | | | | | |

| | | | | | | | | | | | | | | | | |
|---|---|---|---|---|---|---|---|---|---|---|---|---|---|---|---|---|
| aaa | cgc | ttc | ttc | gaa | acc | ggc | ggt | aaa | agc | ctg | ctc | gac | ggc | ctc | aca | 480 |
| Lys | Arg | Phe | Phe | Glu | Thr | Gly | Gly | Lys | Ser | Leu | Leu | Asp | Gly | Leu | Thr | |
| 145 | | | | 150 | | | | 155 | | | | 160 | | | | |

| | | | | | | | | | | | | | | | | |
|---|---|---|---|---|---|---|---|---|---|---|---|---|---|---|---|---|
| cat | ctg | gcc | aag | gac | ctg | gta | aac | aac | ggc | ggc | atg | ccg | agc | cag | gtg | 528 |
| His | Leu | Ala | Lys | Asp | Leu | Val | Asn | Asn | Gly | Gly | Met | Pro | Ser | Gln | Val | |
| | | | | 165 | | | | 170 | | | | 175 | | | | |

| | | | | | | | | | | | | | | | | |
|---|---|---|---|---|---|---|---|---|---|---|---|---|---|---|---|---|
| gac | atg | ggc | gct | ttc | gaa | gtc | ggc | aag | agt | ctg | ggg | acg | act | gaa | ggt | 576 |
| Asp | Met | Gly | Ala | Phe | Glu | Val | Gly | Lys | Ser | Leu | Gly | Thr | Thr | Glu | Gly | |
| | | | 180 | | | | 185 | | | | 190 | | | | | |

| | | | | | | | | | | | | | | | | |
|---|---|---|---|---|---|---|---|---|---|---|---|---|---|---|---|---|
| gca | gtg | gtt | ttc | cgc | aac | gac | gtc | ctc | gaa | ttg | atc | cag | tac | cgg | ccg | 624 |
| Ala | Val | Val | Phe | Arg | Asn | Asp | Val | Leu | Glu | Leu | Ile | Gln | Tyr | Arg | Pro | |
| | | 195 | | | | 200 | | | | 205 | | | | | | |

| | | | | | | | | | | | | | | | | |
|---|---|---|---|---|---|---|---|---|---|---|---|---|---|---|---|---|
| acc | acc | gaa | cag | gtg | cat | gag | cga | ccg | ctg | ctg | gtg | gtc | cca | ccg | cag | 672 |
| Thr | Thr | Glu | Gln | Val | His | Glu | Arg | Pro | Leu | Leu | Val | Val | Pro | Pro | Gln | |
| | 210 | | | | 215 | | | | 220 | | | | | | | |

| | | | | | | | | | | | | | | | | |
|---|---|---|---|---|---|---|---|---|---|---|---|---|---|---|---|---|
| atc | aac | aag | ttt | tat | gtg | ttt | gac | ctg | agc | ccg | gat | aaa | agc | ctg | gcg | 720 |
| Ile | Asn | Lys | Phe | Tyr | Val | Phe | Asp | Leu | Ser | Pro | Asp | Lys | Ser | Leu | Ala | |
| 225 | | | | 230 | | | | 235 | | | | 240 | | | | |

| | | | | | | | | | | | | | | | | |
|---|---|---|---|---|---|---|---|---|---|---|---|---|---|---|---|---|
| cgc | ttc | tgc | ctg | agc | aac | aac | cag | caa | acc | ttt | atc | gtc | agc | tgg | cgc | 768 |
| Arg | Phe | Cys | Leu | Ser | Asn | Asn | Gln | Gln | Thr | Phe | Ile | Val | Ser | Trp | Arg | |
| | | | | 245 | | | | 250 | | | | 255 | | | | |

| | | | | | | | | | | | | | | | | |
|---|---|---|---|---|---|---|---|---|---|---|---|---|---|---|---|---|
| aac | ccg | acc | aag | gcc | cag | cgt | gag | tgg | ggt | ctg | tcg | act | tac | atc | gat | 816 |
| Asn | Pro | Thr | Lys | Ala | Gln | Arg | Glu | Trp | Gly | Leu | Ser | Thr | Tyr | Ile | Asp | |
| | | | 260 | | | | 265 | | | | 270 | | | | | |

| | | | | | | | | | | | | | | | | |
|---|---|---|---|---|---|---|---|---|---|---|---|---|---|---|---|---|
| gcg | ctc | aaa | gaa | gcc | gtc | gac | gta | gtt | tcc | gcc | atc | acc | ggc | agc | aaa | 864 |
| Ala | Leu | Lys | Glu | Ala | Val | Asp | Val | Val | Ser | Ala | Ile | Thr | Gly | Ser | Lys | |
| | | 275 | | | | 280 | | | | 285 | | | | | | |

| | | | | | | | | | | | | | | | | |
|---|---|---|---|---|---|---|---|---|---|---|---|---|---|---|---|---|
| gac | atc | aac | atg | ctc | ggc | gcc | tgc | tcc | ggt | ggc | att | acc | tgc | acc | gcg | 912 |
| Asp | Ile | Asn | Met | Leu | Gly | Ala | Cys | Ser | Gly | Gly | Ile | Thr | Cys | Thr | Ala | |
| | 290 | | | | 295 | | | | 300 | | | | | | | |

| | | | | | | | | | | | | | | | | |
|---|---|---|---|---|---|---|---|---|---|---|---|---|---|---|---|---|
| ctg | ctg | ggt | cac | tac | gcc | gct | ctc | ggc | gag | aag | aag | gtc | aat | gcc | ctg | 960 |
| Leu | Leu | Gly | His | Tyr | Ala | Ala | Leu | Gly | Glu | Lys | Lys | Val | Asn | Ala | Leu | |
| 305 | | | | 310 | | | | 315 | | | | 320 | | | | |

| | | | | | | | | | | | | | | | | |
|---|---|---|---|---|---|---|---|---|---|---|---|---|---|---|---|---|
| acc | ctt | ttg | gtc | agc | gtg | ctc | gac | acc | acc | ctc | gac | tcc | cag | gtt | gca | 1008 |
| Thr | Leu | Leu | Val | Ser | Val | Leu | Asp | Thr | Thr | Leu | Asp | Ser | Gln | Val | Ala | |
| | | | | 325 | | | | 330 | | | | 335 | | | | |

```
ctg ttc gtc gat gag aaa acc ctg gaa gct gcc aag cgt cac tcg tat    1056
Leu Phe Val Asp Glu Lys Thr Leu Glu Ala Ala Lys Arg His Ser Tyr
            340                 345                 350 cag gcc ggc gtg ctg gaa ggc cgc gac atg gcc aaa gtc ttc gcc tgg    1104
Gln Ala Gly Val Leu Glu Gly Arg Asp Met Ala Lys Val Phe Ala Trp
        355                 360                 365 atg cgc cct aac gac ctg atc tgg aac tac tgg gtc aac aac tac ctg    1152
Met Arg Pro Asn Asp Leu Ile Trp Asn Tyr Trp Val Asn Asn Tyr Leu
    370                 375                 380 ctg ggt aac gag cca ccg gtc ttc gac att ctt ttc tgg aac aac gac    1200
Leu Gly Asn Glu Pro Pro Val Phe Asp Ile Leu Phe Trp Asn Asn Asp
385                 390                 395                 400 acc acc cgg ttg cct gct gcg ttc cac ggc gat ctg atc gaa atg ttc    1248
Thr Thr Arg Leu Pro Ala Ala Phe His Gly Asp Leu Ile Glu Met Phe
                405                 410                 415 aaa aat aac cca ctg gtg cgc gcc aat gca ctc gaa gtg agc ggc acg    1296
Lys Asn Asn Pro Leu Val Arg Ala Asn Ala Leu Glu Val Ser Gly Thr
            420                 425                 430 ccg atc gac ctc aaa cag gtc act gcc gac atc tac tcc ctg gcc ggc    1344
Pro Ile Asp Leu Lys Gln Val Thr Ala Asp Ile Tyr Ser Leu Ala Gly
        435                 440                 445 acc aac gat cac atc acg ccc tgg aag tct tgc tac aag tcg gcg caa    1392
Thr Asn Asp His Ile Thr Pro Trp Lys Ser Cys Tyr Lys Ser Ala Gln
    450                 455                 460 ctg ttc ggt ggc aag gtc gaa ttc gtg ctg tcc agc agt ggg cat atc    1440
Leu Phe Gly Gly Lys Val Glu Phe Val Leu Ser Ser Ser Gly His Ile
465                 470                 475                 480 cag agc att ctg aac ccg ccg ggc aat ccg aaa tca cgt tac atg acc    1488
Gln Ser Ile Leu Asn Pro Pro Gly Asn Pro Lys Ser Arg Tyr Met Thr
                485                 490                 495 agc acc gac atg cca gcc acc gcc aac gag tgg caa gaa aac tca acc    1536
Ser Thr Asp Met Pro Ala Thr Ala Asn Glu Trp Gln Glu Asn Ser Thr
            500                 505                 510 aag cac acc gac tcc tgg tgg ctg cac tgg cag gcc tgg cag gcc gag    1584
Lys His Thr Asp Ser Trp Trp Leu His Trp Gln Ala Trp Gln Ala Glu
        515                 520                 525 cgc tcg ggc aaa ctg aaa aag tcc ccg acc agc ctg ggc aac aag gcc    1632
Arg Ser Gly Lys Leu Lys Lys Ser Pro Thr Ser Leu Gly Asn Lys Ala
    530                 535                 540 tat ccg tca gga gaa gcc gcg ccg ggc acg tat gtg cat gaa cgt taa    1680
Tyr Pro Ser Gly Glu Ala Ala Pro Gly Thr Tyr Val His Glu Arg
545                 550                 555

<210> SEQ ID NO 4
<211> LENGTH: 559
<212> TYPE: PRT
<213> ORGANISM: Pseudomonas sp.
<220> FEATURE:
<223> OTHER INFORMATION: 61-3

<400> SEQUENCE: 4

Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
            20                  25                  30

Thr Ser Ala Arg Met Val Leu Thr Gln Ala Ile Lys Gln Pro Ile His
        35                  40                  45

Ser Val Lys His Val Ala His Phe Gly Ile Glu Leu Lys Asn Val Met
    50                  55                  60
```

```
Phe Gly Lys Ser Lys Leu Gln Pro Glu Ser Asp Arg Arg Phe Asn
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Val Ser Ala Ile Thr Gly Ser Lys
        275                 280                 285

Asp Ile Asn Met Leu Gly Ala Cys Ser Gly Gly Ile Thr Cys Thr Ala
    290                 295                 300

Leu Leu Gly His Tyr Ala Ala Leu Gly Glu Lys Lys Val Asn Ala Leu
305                 310                 315                 320

Thr Leu Leu Val Ser Val Leu Asp Thr Thr Leu Asp Ser Gln Val Ala
                325                 330                 335

Leu Phe Val Asp Glu Lys Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Asn Asn Pro Leu Val Arg Ala Asn Ala Leu Glu Val Ser Gly Thr
            420                 425                 430

Pro Ile Asp Leu Lys Gln Val Thr Ala Asp Ile Tyr Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Lys Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
```

```
                   485                 490                 495
Ser Thr Asp Met Pro Ala Thr Ala Asn Glu Trp Gln Glu Asn Ser Thr
            500                 505                 510

Lys His Thr Asp Ser Trp Trp Leu His Trp Gln Ala Trp Gln Ala Glu
        515                 520                 525

Arg Ser Gly Lys Leu Lys Ser Pro Thr Ser Leu Gly Asn Lys Ala
    530                 535                 540

Tyr Pro Ser Gly Glu Ala Ala Pro Gly Thr Tyr Val His Glu Arg
545                 550                 555

<210> SEQ ID NO 5
<211> LENGTH: 1785
<212> TYPE: DNA
<213> ORGANISM: Aeromonas caviae
<220> FEATURE:
<221> NAME/KEY: CDS
<222> LOCATION: (1)..(1782)

<400> SEQUENCE: 5
```

| | | | | | | | | | | | | | | | | |
|---|---|---|---|---|---|---|---|---|---|---|---|---|---|---|---|---|
| atg | agc | caa | cca | tct | tat | ggc | ccg | ctg | ttc | gag | gcc | ctg | gcc | cac | tac | 48 |
| Met | Ser | Gln | Pro | Ser | Tyr | Gly | Pro | Leu | Phe | Glu | Ala | Leu | Ala | His | Tyr | |
| 1 | | | | 5 | | | | | 10 | | | | | 15 | | |
| aat | gac | aag | ctg | ctg | gcc | atg | gcc | aag | gcc | cag | aca | gag | cgc | acc | gcc | 96 |
| Asn | Asp | Lys | Leu | Leu | Ala | Met | Ala | Lys | Ala | Gln | Thr | Glu | Arg | Thr | Ala | |
| | | | 20 | | | | | 25 | | | | | 30 | | | |
| cag | gcg | ctg | ctg | cag | acc | aat | ctg | gac | gat | ctg | ggc | cag | gtg | ctg | gag | 144 |
| Gln | Ala | Leu | Leu | Gln | Thr | Asn | Leu | Asp | Asp | Leu | Gly | Gln | Val | Leu | Glu | |
| | | 35 | | | | | 40 | | | | | 45 | | | | |
| cag | ggc | agc | cag | caa | ccc | tgg | cag | ctg | atc | cag | gcc | cag | atg | aac | tgg | 192 |
| Gln | Gly | Ser | Gln | Gln | Pro | Trp | Gln | Leu | Ile | Gln | Ala | Gln | Met | Asn | Trp | |
| | 50 | | | | | 55 | | | | | 60 | | | | | |
| tgg | cag | gat | cag | ctc | aag | ctg | atg | cag | cac | acc | ctg | ctc | aaa | agc | gca | 240 |
| Trp | Gln | Asp | Gln | Leu | Lys | Leu | Met | Gln | His | Thr | Leu | Leu | Lys | Ser | Ala | |
| 65 | | | | | 70 | | | | | 75 | | | | | 80 | |
| ggc | cag | ccg | agc | gag | ccg | gtg | atc | acc | ccg | gag | cgc | agc | gat | cgc | cgc | 288 |
| Gly | Gln | Pro | Ser | Glu | Pro | Val | Ile | Thr | Pro | Glu | Arg | Ser | Asp | Arg | Arg | |
| | | | | 85 | | | | | 90 | | | | | 95 | | |
| ttc | aag | gcc | gag | gcc | tgg | agc | gaa | caa | ccc | atc | tat | gac | tac | ctc | aag | 336 |
| Phe | Lys | Ala | Glu | Ala | Trp | Ser | Glu | Gln | Pro | Ile | Tyr | Asp | Tyr | Leu | Lys | |
| | | | 100 | | | | | 105 | | | | | 110 | | | |
| cag | tcc | tac | ctg | ctc | acc | gcc | agg | cac | ctg | ctg | gcc | tcg | gtg | gat | gcc | 384 |
| Gln | Ser | Tyr | Leu | Leu | Thr | Ala | Arg | His | Leu | Leu | Ala | Ser | Val | Asp | Ala | |
| | | 115 | | | | | 120 | | | | | 125 | | | | |
| ctg | gag | ggc | gtc | ccc | cag | aag | agc | cgg | gag | cgg | ctg | cgt | ttc | ttc | acc | 432 |
| Leu | Glu | Gly | Val | Pro | Gln | Lys | Ser | Arg | Glu | Arg | Leu | Arg | Phe | Phe | Thr | |
| | 130 | | | | | 135 | | | | | 140 | | | | | |
| cgc | cag | tac | gtc | aac | gcc | atg | gcc | ccc | agc | aac | ttc | ctg | gcc | acc | aac | 480 |
| Arg | Gln | Tyr | Val | Asn | Ala | Met | Ala | Pro | Ser | Asn | Phe | Leu | Ala | Thr | Asn | |
| 145 | | | | | 150 | | | | | 155 | | | | | 160 | |
| ccc | gag | ctg | ctc | aag | ctg | acc | ctg | gag | tcc | gac | ggc | cag | aac | ctg | gtg | 528 |
| Pro | Glu | Leu | Leu | Lys | Leu | Thr | Leu | Glu | Ser | Asp | Gly | Gln | Asn | Leu | Val | |
| | | | | 165 | | | | | 170 | | | | | 175 | | |
| cgc | gga | ctg | gcc | ctc | ttg | gcc | gag | gat | ctg | gag | cgc | agc | gcc | gat | cag | 576 |
| Arg | Gly | Leu | Ala | Leu | Leu | Ala | Glu | Asp | Leu | Glu | Arg | Ser | Ala | Asp | Gln | |
| | | | 180 | | | | | 185 | | | | | 190 | | | |
| ctc | aac | atc | cgc | ctg | acc | gac | gaa | tcc | gcc | ttc | gag | ctc | ggg | cgg | gat | 624 |
| Leu | Asn | Ile | Arg | Leu | Thr | Asp | Glu | Ser | Ala | Phe | Glu | Leu | Gly | Arg | Asp | |
| | | 195 | | | | | 200 | | | | | 205 | | | | |
| ctg | gcc | ctg | acc | ccg | ggc | cgg | gtg | gtg | cag | cgc | acc | gag | ctc | tat | gag | 672 |
| Leu | Ala | Leu | Thr | Pro | Gly | Arg | Val | Val | Gln | Arg | Thr | Glu | Leu | Tyr | Glu | |

|  |  |  |  |  |  |  |  |  |  |  |  |  |  |  |  |
|---|---|---|---|---|---|---|---|---|---|---|---|---|---|---|---|
|  |  | 210 |  |  |  | 215 |  |  |  | 220 |  |  |  |  |  |
| ctc | att | cag | tac | agc | ccg | act | acc | gag | acg | gtg | ggc | aag | aca | cct | gtg | 720 |
| Leu | Ile | Gln | Tyr | Ser | Pro | Thr | Thr | Glu | Thr | Val | Gly | Lys | Thr | Pro | Val |  |
| 225 |  |  |  |  | 230 |  |  |  |  | 235 |  |  |  |  | 240 |  |
| ctg | ata | gtg | ccg | ccc | ttc | atc | aac | aag | tac | tac | atc | atg | gac | atg | cgg | 768 |
| Leu | Ile | Val | Pro | Pro | Phe | Ile | Asn | Lys | Tyr | Tyr | Ile | Met | Asp | Met | Arg |  |
|  |  |  |  | 245 |  |  |  |  | 250 |  |  |  |  | 255 |  |  |
| ccc | cag | aac | tcc | ctg | gtc | gcc | tgg | ctg | gtc | gcc | cag | ggc | cag | acg | gta | 816 |
| Pro | Gln | Asn | Ser | Leu | Val | Ala | Trp | Leu | Val | Ala | Gln | Gly | Gln | Thr | Val |  |
|  |  |  | 260 |  |  |  |  | 265 |  |  |  |  | 270 |  |  |  |
| ttc | atg | atc | tcc | tgg | cgc | aac | ccg | ggc | gtg | gcc | cag | gcc | caa | atc | gat | 864 |
| Phe | Met | Ile | Ser | Trp | Arg | Asn | Pro | Gly | Val | Ala | Gln | Ala | Gln | Ile | Asp |  |
|  |  | 275 |  |  |  |  | 280 |  |  |  |  | 285 |  |  |  |  |
| ctc | gac | gac | tac | gtg | gtg | gat | ggc | gtc | atc | gcc | gcc | ctg | gac | ggc | gtg | 912 |
| Leu | Asp | Asp | Tyr | Val | Val | Asp | Gly | Val | Ile | Ala | Ala | Leu | Asp | Gly | Val |  |
| 290 |  |  |  |  | 295 |  |  |  |  | 300 |  |  |  |  |  |  |
| gag | gcg | gcc | acc | ggc | gag | cgg | gag | gtg | cac | ggc | atc | ggc | tac | tgc | atc | 960 |
| Glu | Ala | Ala | Thr | Gly | Glu | Arg | Glu | Val | His | Gly | Ile | Gly | Tyr | Cys | Ile |  |
| 305 |  |  |  |  | 310 |  |  |  |  | 315 |  |  |  |  | 320 |  |
| ggc | ggc | acc | gcc | ctg | tcg | ctc | gcc | atg | ggc | tgg | ctg | gcg | gcg | cgg | cgc | 1008 |
| Gly | Gly | Thr | Ala | Leu | Ser | Leu | Ala | Met | Gly | Trp | Leu | Ala | Ala | Arg | Arg |  |
|  |  |  |  | 325 |  |  |  |  | 330 |  |  |  |  | 335 |  |  |
| cag | aag | cag | cgg | gtg | cgc | acc | gcc | acc | ctg | ttc | act | acc | ctg | ctg | gac | 1056 |
| Gln | Lys | Gln | Arg | Val | Arg | Thr | Ala | Thr | Leu | Phe | Thr | Thr | Leu | Leu | Asp |  |
|  |  |  | 340 |  |  |  |  | 345 |  |  |  |  | 350 |  |  |  |
| ttc | tcc | cag | ccc | ggg | gag | ctt | ggc | atc | ttc | atc | cac | gag | ccc | atc | ata | 1104 |
| Phe | Ser | Gln | Pro | Gly | Glu | Leu | Gly | Ile | Phe | Ile | His | Glu | Pro | Ile | Ile |  |
|  |  | 355 |  |  |  |  | 360 |  |  |  |  | 365 |  |  |  |  |
| gcg | gcg | ctc | gag | gcg | caa | aat | gag | gcc | aag | ggc | atc | atg | gac | ggg | cgc | 1152 |
| Ala | Ala | Leu | Glu | Ala | Gln | Asn | Glu | Ala | Lys | Gly | Ile | Met | Asp | Gly | Arg |  |
| 370 |  |  |  |  | 375 |  |  |  |  | 380 |  |  |  |  |  |  |
| cag | ctg | gcg | gtc | tcc | ttc | agc | ctg | ctg | cgg | gag | aac | agc | ctc | tac | tgg | 1200 |
| Gln | Leu | Ala | Val | Ser | Phe | Ser | Leu | Leu | Arg | Glu | Asn | Ser | Leu | Tyr | Trp |  |
| 385 |  |  |  |  | 390 |  |  |  |  | 395 |  |  |  |  | 400 |  |
| aac | tac | tac | atc | gac | agc | tac | ctc | aag | ggt | cag | agc | ccg | gtg | gcc | ttc | 1248 |
| Asn | Tyr | Tyr | Ile | Asp | Ser | Tyr | Leu | Lys | Gly | Gln | Ser | Pro | Val | Ala | Phe |  |
|  |  |  |  | 405 |  |  |  |  | 410 |  |  |  |  | 415 |  |  |
| gat | ctg | ctg | cac | tgg | aac | agc | gac | agc | acc | aat | gtg | gcg | ggc | aag | acc | 1296 |
| Asp | Leu | Leu | His | Trp | Asn | Ser | Asp | Ser | Thr | Asn | Val | Ala | Gly | Lys | Thr |  |
|  |  |  | 420 |  |  |  |  | 425 |  |  |  |  | 430 |  |  |  |
| cac | aac | agc | ctg | ctg | cgc | cgt | ctc | tac | ctg | gag | aac | cag | ctg | gtg | aag | 1344 |
| His | Asn | Ser | Leu | Leu | Arg | Arg | Leu | Tyr | Leu | Glu | Asn | Gln | Leu | Val | Lys |  |
|  |  | 435 |  |  |  |  | 440 |  |  |  |  | 445 |  |  |  |  |
| ggg | gag | ctc | aag | atc | cgc | aac | acc | cgc | atc | gat | ctc | ggc | aag | gtg | aag | 1392 |
| Gly | Glu | Leu | Lys | Ile | Arg | Asn | Thr | Arg | Ile | Asp | Leu | Gly | Lys | Val | Lys |  |
| 450 |  |  |  |  | 455 |  |  |  |  | 460 |  |  |  |  |  |  |
| acc | cct | gtg | ctg | ctg | gtg | tcg | gcg | gtg | gac | gat | cac | atc | gcc | ctc | tgg | 1440 |
| Thr | Pro | Val | Leu | Leu | Val | Ser | Ala | Val | Asp | Asp | His | Ile | Ala | Leu | Trp |  |
| 465 |  |  |  |  | 470 |  |  |  |  | 475 |  |  |  |  | 480 |  |
| cag | ggc | acc | tgg | cag | ggc | atg | aag | ctg | ttt | ggc | ggg | gag | cag | cgc | ttc | 1488 |
| Gln | Gly | Thr | Trp | Gln | Gly | Met | Lys | Leu | Phe | Gly | Gly | Glu | Gln | Arg | Phe |  |
|  |  |  |  | 485 |  |  |  |  | 490 |  |  |  |  | 495 |  |  |
| ctc | ctg | gcg | gag | tcc | ggc | cac | atc | gcc | ggc | atc | atc | aac | ccg | ccg | gcc | 1536 |
| Leu | Leu | Ala | Glu | Ser | Gly | His | Ile | Ala | Gly | Ile | Ile | Asn | Pro | Pro | Ala |  |
|  |  |  |  | 500 |  |  |  |  | 505 |  |  |  |  | 510 |  |  |
| gcc | aac | aag | tac | ggc | ttc | tgg | cac | aac | ggg | gcc | gag | gcc | gag | agc | ccg | 1584 |
| Ala | Asn | Lys | Tyr | Gly | Phe | Trp | His | Asn | Gly | Ala | Glu | Ala | Glu | Ser | Pro |  |
|  |  |  |  | 515 |  |  |  |  | 520 |  |  |  |  | 525 |  |  |
| gag | agc | tgg | ctg | gca | ggg | gcg | acg | cac | cag | ggc | ggc | tcc | tgg | tgg | ccc | 1632 |

```
Glu Ser Trp Leu Ala Gly Ala Thr His Gln Gly Gly Ser Trp Trp Pro
                530                 535                 540 gag atg atg ggc ttt atc cag aac cgt gac gaa ggg tca gag ccc gtc    1680
Glu Met Met Gly Phe Ile Gln Asn Arg Asp Glu Gly Ser Glu Pro Val
545                 550                 555                 560 ccc gcg cgg gtc ccg gag gaa ggg ctg gcc ccc gcc ccc ggc cac tat    1728
Pro Ala Arg Val Pro Glu Glu Gly Leu Ala Pro Ala Pro Gly His Tyr
                565                 570                 575 gtc aag gtg cgg ctc aac ccc gtg ttt gcc tgc cca aca gag gag gac    1776
Val Lys Val Arg Leu Asn Pro Val Phe Ala Cys Pro Thr Glu Glu Asp
                580                 585                 590 gcc gca tga                                                         1785
Ala Ala <210> SEQ ID NO 6
<211> LENGTH: 594
<212> TYPE: PRT
<213> ORGANISM: Aeromonas caviae

<400> SEQUENCE: 6

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
                20                  25                  30

Gln Ala Leu Leu Gln Thr Asn Leu Asp Asp Leu Gly Gln Val Leu Glu
            35                  40                  45

Gln Gly Ser Gln Gln Pro Trp Gln Leu Ile Gln Ala Gln Met Asn Trp
        50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
                100                 105                 110

Gln Ser Tyr Leu Leu Thr Ala Arg His Leu Leu Ala Ser Val Asp Ala
            115                 120                 125

Leu Glu Gly Val Pro Gln Lys Ser Arg Glu Arg Leu Arg Phe Phe Thr
        130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
                180                 185                 190

Leu Asn Ile Arg Leu Thr Asp Glu Ser Ala Phe Glu Leu Gly Arg Asp
            195                 200                 205

Leu Ala Leu Thr Pro Gly Arg Val Val Gln Arg Thr Glu Leu Tyr Glu
        210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
            275                 280                 285
```

```
Leu Asp Asp Tyr Val Val Asp Gly Val Ile Ala Ala Leu Asp Gly Val
    290             295             300
Glu Ala Ala Thr Gly Glu Arg Glu Val His Gly Ile Gly Tyr Cys Ile
305             310              315                 320
Gly Gly Thr Ala Leu Ser Leu Ala Met Gly Trp Leu Ala Arg Arg
                325             330                 335
Gln Lys Gln Arg Val Arg Thr Ala Thr Leu Phe Thr Thr Leu Leu Asp
            340             345                 350
Phe Ser Gln Pro Gly Glu Leu Gly Ile Phe Ile His Glu Pro Ile Ile
        355             360             365
Ala Ala Leu Glu Ala Gln Asn Glu Ala Lys Gly Ile Met Asp Gly Arg
    370             375             380
Gln Leu Ala Val Ser Phe Ser Leu Leu Arg Glu Asn Ser Leu Tyr Trp
385             390             395                 400
Asn Tyr Tyr Ile Asp Ser Tyr Leu Lys Gly Gln Ser Pro Val Ala Phe
                405             410              415
Asp Leu Leu His Trp Asn Ser Asp Ser Thr Asn Val Ala Gly Lys Thr
            420             425                 430
His Asn Ser Leu Leu Arg Arg Leu Tyr Leu Glu Asn Gln Leu Val Lys
            435             440                 445
Gly Glu Leu Lys Ile Arg Asn Thr Arg Ile Asp Leu Gly Lys Val Lys
    450             455             460
Thr Pro Val Leu Leu Val Ser Ala Val Asp Asp His Ile Ala Leu Trp
465             470             475                 480
Gln Gly Thr Trp Gln Gly Met Lys Leu Phe Gly Gly Glu Gln Arg Phe
                485             490                 495
Leu Leu Ala Glu Ser Gly His Ile Ala Gly Ile Ile Asn Pro Pro Ala
            500             505             510
Ala Asn Lys Tyr Gly Phe Trp His Asn Gly Ala Glu Ala Glu Ser Pro
        515             520             525
Glu Ser Trp Leu Ala Gly Ala Thr His Gln Gly Gly Ser Trp Trp Pro
    530             535             540
Glu Met Met Gly Phe Ile Gln Asn Arg Asp Glu Gly Ser Glu Pro Val
545             550             555                 560
Pro Ala Arg Val Pro Glu Glu Gly Leu Ala Pro Ala Pro Gly His Tyr
                565             570             575
Val Lys Val Arg Leu Asn Pro Val Phe Ala Cys Pro Thr Glu Glu Asp
            580             585                 590
Ala Ala
```

US 9,447,441 B2

METHOD FOR PRODUCING POLYHYDROXYALKANOATE HAVING LONG MAIN CHAIN STRUCTURE

SEQUENCE LISTING

The instant application contains a Sequence Listing which has been submitted electronically in ASCII format and is hereby incorporated by reference in its entirety. Said ASCII copy, created on Apr. 22, 2014, is named P45393_SL.txt and is 41,078 bytes in size.

TECHNICAL FIELD

The present invention relates to a method for producing a polyhydroxyalkanoate (PHA) having a long main chain structure and a polymer obtained by the method.

BACKGROUND ART

Most bacteria use sugars and vegetable oils, which are biomass, as source, and accumulate polyhydroxyalkanoates (PHAs) as energy storage materials in cells (Non Patent Literatures 1 to 3). Since PHAs have biodegradable and thermoplastic properties, they are expected to be applied as an alternative to petroleum-based plastic (Non Patent Literatures 4 and 5).

In addition, since PHAs have biodegradable and biocompatible properties, they are also expected to be applied as biomaterial (Non Patent Literatures 6 and 7). It has been reported that PHAs have high affinities with bone and cartilage tissues (Non Patent Literature 8), blood (Non Patent Literature 9), and various cell lines through in vivo and in vitro experiments, and PHAs are expected to be used in the medical field.

Intracellular synthesis of a PHA in a microbial cell is carried out by supplying a hydroxyacyl-CoA as a monomer from the metabolic pathway using carbon source as source and polymerizing the supplied monomer by a PHA synthase. As such, the intracellular synthesis of the PHA is characterized in that all of the reactions including supplying a monomer and synthesizing a polymer are carried out in the microbial cell. In the present system, a kind or composition of the monomer constituting the PHA is determined by a kind of the carbon source to be supplied, the metabolic pathway, and substrate specificity of the PHA synthase. In order to adjust these factors, culture conditions and carbon sources have been adjusted, and new metabolic pathways have been established by combining genetic engineering methods and metabolic engineering methods, and thus, more than 100 kinds of PHA families have been reported so far (Non Patent Literature 10). Most of the reported PHA families are PHAs having a variety of side chains. As PHAs having a variety of main chains, only a few PHAs such as lactate (Non Patent Literature 11), 4-hydroxybutyrate (4HB) (Non Patent Literature 12), 4-hydroxyvalerate (4HV) (Non Patent Literature 13), 5-hydroxyvalerate (5HV) (Non Patent Literature 14), and 6-hydroxyhexanoate (6HH) have been reported.

CITATION LIST

Non Patent Literature

Non Patent Literature 1: Doi, Y.; Kitamura, S.; Abe, H., Macromolecules 1995, 28, 4822-4828.

Non Patent Literature 2: Steinbuchel, A.; Fuchtenbusch, B., Trends in Biotechnology 1998, 16, 419-427.
Non Patent Literature 3: Rehm, B. H. A.; Steinbuchel, A., Int. J. Biol. Macromol. 1999, 25, 3-19.
Non Patent Literature 4: Chen, G. Q. Chemical Society Reviews 2009, 38, 2434-2446.
Non Patent Literature 5: Sudesh, K.; Abe, H.; Doi, Y., Progress in Polymer Science 2000, 25, 1503-1555.
Non Patent Literature 6: Chen, G. Q.; Wu, Q.; Wang, Y., Artificial Cells Blood Substitutes and Biotechnology 2009, 37, 1-12.
Non Patent Literature 7: Boccaccini, A. R.; Misra, S. K.; Valappil, S. P.; Roy, I., Biomacromolecules 2006, 7, 2249-2258.
Non Patent Literature 8: Gogolewski, S.; Jovanovic, M.; Perren, S. M.; Dillon, J. G.; Hughes, M. K., Journal of Biomedical Materials Research 1993, 27, 1135-1148.
Non Patent Literature 9: Deng, Y.; Lin, X. S.; Zheng, Z.; Deng, J. G.; Chen, J. C.; Ma, H.; Chen, G. Q. Biomaterials 2003, 24, 4273-4281.
Non Patent Literature 10: Steinbuchel, A.; Valentin, H. E., Ferns Microbiology Letters 1995, 128, 219-228.
Non Patent Literature 11: Taguchi, S.; Yamada, M.; Matsumoto, K.; Tajima, K.; Satoh, Y.; Munekata, M.; Ohno, K.; Kohda, K.; Shimamura, T.; Kambe, H.; Obata, S., Proc. Natl. Acad. Sci. U.S.A. 2008, 105, 17323-7.
Non Patent Literature 12: Kunioka, M.; Nakamura, Y.; Doi, Y., Polymer Communications 1988, 29, 174-176.
Non Patent Literature 13: Gorenflo, V.; Schrnack, G.; Vogel, R.; Steinbuchel, A., Biomacromolecules 2001, 2, 45-57.
Non Patent Literature 14: Doi, Y.; Tamaki, A.; Kunioka, M.; Soga, K., Makromol. Chem., Rapid Commun 1987, 8, 631-635.

SUMMARY OF INVENTION

Technical Problem

Among various PHAs, PHAs having a long main chain monomer are expected to be improved in biodegradable properties. For example, it is known that P(3HB-co-4HB) copolymers, which include 4HB units having no side chain and one more carbon atom in the main chain, as compared with 3-hydroxybutyrate (3HB) as a monomer structure of a basic PHA, exhibits enzymatic degradable properties by PHA depolymerases and also lipases (Chen, G. Q.; Wu, Q.; Wang, Y., Artificial Cells Blood Substitutes and Biotechnology 2009, 37, 1-12 and Saito, Y.; Doi, Y., International Journal of Biological Macromolecules 1994, 16, 99-104.). A P(3HB) homopolymer having a side chain or other PHAs do not exhibit a degradable properties by lipases. Therefore, the enzymatic degradable properties of the P(3HB-co-4HB) copolymers by lipases is special properties.

In addition, since lipases are present in cells in vivo, it is expected that biodegradable properties in cells can be improved by the PHAs having biodegradable properties by lipases. Therefore, improved biodegradable properties in cells are useful when a PHA is used as a tissue medical material or used for drug delivery.

One of the reasons why 4HB exhibits the degradable properties by lipases may be that 4HB is a monomer which does not have a side chain structure but have a linear structure and thus can be easily attacked by enzymes.

Based on the above-described understandings, it is expected that a PHA including a monomer (5HV, 6HH, or the like) having a longer main chain is further improved in degradable properties by lipases. However, efficient synthesis of a PHA including a 5HV unit and evaluation of enzymatic degradable properties thereof have not been carried out so far.

Therefore, in view of the foregoing circumstance, an object of the present invention is to provide an efficient method for producing a PHA including a 5HV unit to create a PHA to be usefully used as a bioplastic or a biomaterial.

Solution to Problem

As a result of careful research to solve the above-described problem, it was found that when a microorganism belonging to Ralstonia genus was cultured in a culture medium including lactone and/or hydroxy acid or salt of hydroxy acid as carbon source, a PHA including a 5HV unit was produced, so that the present invention was completed.

The present invention includes the following.

(1) A method for producing a polyhydroxyalkanoate (PHA) including at least a 5-hydroxyvalerate (5HV) unit, comprising: culturing a microorganism belonging to Ralstonia genus in a culture medium including lactone having 12 or more carbon atoms constituting a ring and/or a hydroxy acid or a salt of hydroxy acid as a carbon source.

(2) The method described in the paragraph (1), in which the microorganism belonging to Ralstonia genus is Ralstonia eutropha to which a gene encoding a polyhydroxyalkanoate synthase is introduced.

(3) The method described in the paragraph (2), in which the gene encoding a polyhydroxyalkanoate synthase encodes a protein as described in the following paragraph (a) or (b).

(a) A protein comprising an amino acid sequence set forth in any one of SEQ ID NOS: 2, 4, and 6.

(b) A protein comprising an amino acid sequence in which one or several amino acids in the amino acid sequence of the protein described in the paragraph (a) are deleted, substituted, or added, and having a polyhydroxyalkanoate synthetic activity.

(4) The method described in any one of the paragraphs (1) to (3), in which the lactone is ω-pentadecalactone.

(5) The method described in any one of the paragraphs (1) to (4), in which the salt of hydroxy acid is a 5-hydroxyvalerate salt.

(6) The method described in any one of the paragraphs (1) to (5), in which the polyhydroxyalkanoate further includes a 3-hydroxybutyrate (3HB) unit.

(7) The method described in any one of the paragraphs (1) to (6), in which the polyhydroxyalkanoate is a polyhydroxyalkanoate copolymer including 10 to 35 mol % 5-hydroxyvalerate units.

The present specification incorporates herein the contents described in the specification and/or the drawings of JP Patent Application No. 2011-193230 as a base for claiming the benefit of priority of the present application.

Advantageous Effects of Invention

According to the present invention, it is possible to produce PHAs including 5HV units which are useful as bioplastics and also biocompatible materials.

BRIEF DESCRIPTION OF DRAWINGS

In FIGS. 4(A) and 4(B), P(3HB-co-3HP-co-5HV) of 5% 3HP 1% 5HV: P(3HB-co-5 mol % 3HP-co-1 mol % 5HV), 5% 3HP 10% 5HV: P(3HB-co-5 mol % 3HP-co-10 mol % 5HV), 18% 3HP 5% 5HV: P(3HB-co-18 mol % 3HP-co-5 mol % 5HV), and 23% 3HP 6% 5HV: P(3HB-co-23 mol % 3HP-co-6 mol % 5HV) are expressed by Sample Nos. 1, 14, 10, and 11, respectively, listed in Tables 2 and 3. P(3HB) is produced by Ralstonia eutropha H16 from fructose. P(3HP) and P(5HV) are chemically synthesized (Abe, H.; Doi, Y.; Aoki, H.; Akehata, T.; Hori, Y.; Yamaguchi, A., Macromolecules 1995, 28, 7630-7637.). In FIG. 4(B), P(98 mol % 4HB-co-3HB) is produced from 1,4-butanediol by Comainonas acidovorans. In addition, P(3HB-co-9 mol % 3HP-co-14 mol % 5HV) is expressed by a Sample No. 30 or 31 listed in Table 6. Furthermore, P(3HB-co-7 mol % 3HP-co-20 mol % 5HY) is expressed by a Sample No. 22 listed in Table 5.

DESCRIPTION OF EMBODIMENTS

Figure 1:
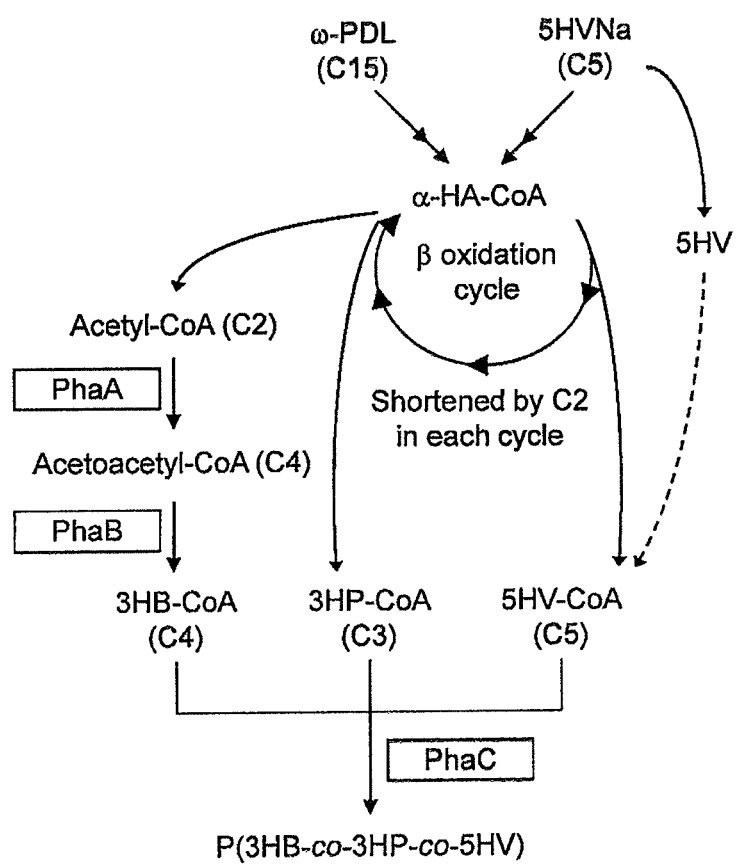
FIG. 1 illustrates a synthetic pathway of P(3HB-co-3HP-co-5HV) of Ralstonia eutropha. 5HV: 5-hydroxyvalerate, 5HVNa: sodium 5-hydroxyvalerate, ω-PDL: ω-pentadecalactone, PhaA: β-ketothiolase, PhaB: NADPH-dependent acetoacetyl-CoA reductase, PhaC: PHA synthase.

Hereinafter, the present invention will be described in detail.

In the previous research, Doi et al. (Doi, Y.; Tamaki, A.; Kunioka, M.; Soga, K., Makromol. Chem., Rapid Commun 1987, 8, 631-635.) synthesized P(3HB-co-3HV-co-5HV) copolymers (herein, 3HV is 3-hydroxyvalerate) from 5-chloro pentanoic acid and pentanoic acid by using *Ralstonia eutropha* H16. This result indicates that *Ralstonia eutropha* has a pathway for supplying 5HV-CoA monomer. However, since the amount of polymers accumulated was very small due to toxicity of 5-chloro pentanoic acid, such a system was not suitable for analyzing the synthesized polymer. Meanwhile, it is known that lactone rings and alkanoate salts have low toxicity to cells (Doi, Y.; Tamaki, A.; Kunioka, M.; Soga, K., Makromol. Chem., Rapid Commun 1987, 8, 631-635.).

Therefore, the present inventors made an attempt to synthesize a PHA including 5HV with a lactone (for example, ω-pentadecalactone (ω-PDL)) or a salt of hydroxy acid (for example, sodium 5-hydroxyvalerate (5HVNa)) as carbon source by using a microorganism such as *Ralstonia eutropha* belonging to *Ralstonia* genus. As a result, it was found that in the microorganism belonging to *Ralstonia* genus, 5HV-CoA can be supplied from the β oxidation pathway and a PHA including 5HV can be synthesized, so that the present invention was completed.

The present invention relates to a method for producing a polyhydroxyalkanoate (PHA) including at least a 5-hydroxyvalerate (5HV) unit by culturing a microorganism belonging to *Ralstonia* genus in a culture medium containing a lactone and/or a hydroxy acid or a salt of hydroxy acid as a carbon source (hereinafter, referred to as "the present method"). In the present method, as the PHA including a 5HV unit, a PHA copolymer including a 3-hydroxybutyrate (3HB) unit and/or a 3-hydroxypropionate (3HP) unit together with the 5HV unit can be produced.

According to the present invention, it is possible to produce a PHA including a high percentage of 5HV units, having degradable properties by lipases, and having low toxicity of the cell. The produced PHA has degradable properties by lipases, and thus, it has biodegradable properties and can be used as a biomaterial.

Examples of the microorganism belonging to *Ralstonia* genus used in the present method include *Ralstonia eutropha* (also called *Cupriavidus necator*), *Ralstonia mannitolilytica*, *Ralstonia metallidurans*, *Ralstonia oxalatica*, *Ralstonia paucula*, *Ralstonia solanacearum*, and the like. Examples of strains of *Ralstonia eutropha* include *Ralstonia eutropha* H16 strain (ATCC No. 17699) (which may be simply referred to as "*Ralstonia eutropha* H16" in the present specification; available from ATCC (American Type Culture Collection)).

Examples of the microorganism belonging to *Ralstonia* genus used in the present method include a microorganism (for example, a recombinant *Ralstonia eutropha*) belonging to *Ralstonia* genus to which a gene encoding a polyhydroxyalkanoate synthase (PHA synthase; PhaC) is introduced. Introducing a PHA synthase highly capable of incorporating 5HV-CoA to a microorganism belonging to *Ralstonia* genus makes possible to produce PHA copolymers having a variety of 5HV unit compositions (for example, PHA copolymers including high percentages of 5HV units).

Examples of the microorganism belonging to *Ralstonia* genus to which a gene encoding a PHA synthase is introduced include *Ralstonia eutropha* PHB-4 strain (DSM No. 541) (which may be simply referred to as "*Ralstonia eutropha* PHB-4" in the present specification; available from DSMZ (German Collection of Microorganisms and Cell Cultures)), which is a PHA synthase gene deletion mutant strain of the *Ralstonia eutropha* H16.

Examples of the gene encoding an PHA synthase to be introduced include a gene encoding a protein comprising an amino acid sequence set forth in any one of SEQ ID NOS: 2, 4, and 6. A protein (nucleotide sequence: SEQ ID NO: 1 (Accession No. AY836680)) comprising the amino acid sequence set forth in SEQ ID NO: 2 (Accession No. AAW65074) is a PHA synthase (Pha$_{Re}$) derived from *Ralstonia eutropha*. A protein (nucleotide sequence: SEQ ID NO: 3 (Accession No. AB014758, Region: 543 . . . 2222)) comprising the amino acid sequence set forth in SEQ ID NO: 4 (Accession No. BAA36200) is a PHA synthase 1 (PhaC1$_{Ps}$) derived from *Pseudomonas* sp. 61-3 strain. A protein (nucleotide sequence: SEQ ID NO: 5 (Accession No. D88825, Region: 2694 . . . 4478)) comprising the amino acid sequence set forth in SEQ ID NO: 6 (Accession No. BAA21815) is a PHA synthase (PhaC$_{Ac}$) derived from *Aeromonas caviae*. Furthermore, a gene encoding a protein comprising an amino acid sequence in which one or several (for example, 1 to 10, preferably 1 to 5, and particularly preferably 1 to 3) amino acids in one of the amino acid sequences of these proteins are deleted, substituted, or added, and having PHA synthetic activity, or a gene encoding a protein comprising an amino acid sequence having, for example, 60% or more, 70% or more, 80% or more, 85% or more, 90% or more, 95% or more, 96% or more, 97% or more, 98% or more, or 99% or more identity with the amino acid sequence of the above-described protein, and having PHA synthetic activity can also be used as a gene encoding a PHA synthase to be introduced. Identity (%) of amino acid sequences can be determined more appropriately by alignment using, for example, a well-known homology search program (for example, BLAST).

Herein, the term "PHA synthetic activity" refers to an activity of synthesizing a PHA polymer through a reaction with hydroxyacyl-CoA as a substrate. For example, the PHA synthetic activity can be evaluated by contacting the PHA synthase with and allowing to react with hydroxyacyl-CoA (for example, 3HB-CoA, 3HP-CoA, 5HV-CoA) as a substrate and determining whether a PHA polymer is produced or not.

In addition, a DNA which hybridizes with a DNA comprising a complementary nucleotide sequence of the DNA encoding the above-described protein under stringent conditions and encodes a protein having a PHA synthetic activity can also be used as a gene encoding a PHA synthase to be introduced. Herein, the term "stringent conditions" refers to conditions under which a so-called specific hybrid is formed. To be specific, the stringent conditions refer to, for example, a concentration of sodium of 300 to 2000 mM, and preferably 600 to 900 mM, and a temperature of 40 to 75° C., and preferably 55 to 65° C. In addition, the stringent conditions can be determined appropriately by referring to general text such as Sambrook et al., Molecular Cloning: A Laboratory Manual, 3rd Ed., Cold Spring Harbor Laboratory Press (2001) and the like.

A gene encoding a PHA synthase can be amplified and isolated by PCR using, for example, genome DNA of the microorganism from which PHA synthases are derived as a template and a specific primer set.

Alternatively, once a nucleotide sequence of a gene encoding a PHA synthase is determined, the gene encoding the PHA synthase can be obtained through a chemical synthesis, a PCR using a cloned probe as a template, or through hybridization using a DNA fragment having the above-described nucleotide sequence as a probe. In addition, a mutant of a gene encoding a PHA synthase, which mutant is a gene encoding a PHA synthase having a function equivalent to that of the PHA synthase encoded by the gene before the mutation, can be synthesized by site-directed mutagenesis or the like. To introduce a mutation into a gene encoding a PHA synthase, known methods such as a Kunkel method and a Gapped duplex method or other methods equivalent thereto may be employed. For example, a mutation is introduced by using a mutagenesis kit utilizing site-directed mutagenesis (for example, Mutant-K (manufactured by TAKARA BIO Inc.) or Mutant-G (manufactured by TAKARA BIO Inc.), or a LA PCR in vitro Mutagenesis Series Kit manufactured by TAKARA BIO Inc.

In order to introduce a gene encoding a PHA synthase to a microorganism belonging to *Ralstonia* genus, an expression vector including the gene encoding the PHA synthase is prepared. The expression vector can be obtained by inserting the gene encoding the PHA synthase into an appropriate vector. Examples of the vector used include pBBR series vectors capable of replicate in gram-negative bacteria. The expression vector may optionally include a control sequence (for example, a promoter, a terminator, and the like) operable in the microorganism belonging to *Ralstonia* genus.

A method for introducing an expression vector into a microorganism belonging to *Ralstonia* genus is not particularly limited as long as the DNA can be introduced into the microorganism belonging to *Ralstonia* genus. Examples include a method using calcium ions, electroporation, and the like.

In the present method, a carbon source in the culture medium is a lactone and/or a hydroxy acid or a salt of hydroxy acid. Examples of the lactone include lactones having 12 or more carbon atoms (for example, 12 to 20, and preferably 14 to 16) constituting a ring, and particularly, ω-pentadecalactone (ω-PDL; also called 15-penta decano-lactone; 15 carbon atoms constituting a ring), or the like. Examples of the hydroxy acid or salt of hydroxy acid include 5-hydroxy valeric acid, 5-hydroxyvalerate salts (for example, sodium 5-hydroxyvalerate (5HVNa)), or the like. A concentration of the lactone and/or hydroxy acid or salt of hydroxy acid in the culture medium can be appropriately determined by a desired content of 5HV units in the PHA to be produced, and may be, for example, 10 to 100 g, and preferably 10 to 50 g, with respect to 1 L of culture medium.

Examples of the culture medium used for culture include inorganic culture media. Examples of compositions of the inorganic culture media include that containing 2.8 g of $KH_2PO_4$, 3.32 g of $Na_2HPO_4$, 0.25 g of $MgSO_2.7H_2O$, and 1 ml of a minor element solution (which contains 20 g of $FeCl_3.6H_2O$, 10 g of $CaCl_2.H_2O$, 0.03 g of $CuSO_4.6H_2O$, 0.05 g of $MnCl_2.4H_2O$, and 0.1 g of $ZnSO_4.7H_2O$ with respect to 1 L of 0.5N HCl) with respect to 1 L of distilled water. Examples of pH of the culture media include 6 to 8, and preferably 7.0 to 7.4.

In the present method, a microorganism belonging to *Ralstonia* genus is cultured in a culture medium containing a lactone and/or a hydroxy acid or a salt of hydroxy acid as a carbon source. Examples of the culture temperature include about 20° C. to about 40° C., and preferably about 25° C. to about 35° C. The culture time is not particularly limited, but examples include about 5 hours to about 48 hours or more.

After culturing, a PHA can be recovered by, for example, lyophilizing the microbial cells; subjecting the lyophilized microbial cell to extraction using an organic solvent such as chloroform; adding to the extract an organic solvent, such as hexane or methanol, in which the PHA is not dissolved, to precipitate the polymer.

According to the present method described above, PHAs including 5HV units (for example, PHA copolymers including 3HB units, 3HP units, and 5HV units (which may be referred to as "P(3HB-co-3HP-co-5HV)" in the present specification)) can be produced in a microorganism belonging to *Ralstonia* genus. P(3HB-co-3HP-co-5HV) produced by the present method may be that comprising 3HB units, 3HP units, and 5HV units. To be specific, the produced P(3HB-co-3HP-co-5HV) may include constituting units represented by the following formula (I) (3HB unit), formula (II) (3HP unit), and formula (III) (5HV).

[Formula 1]

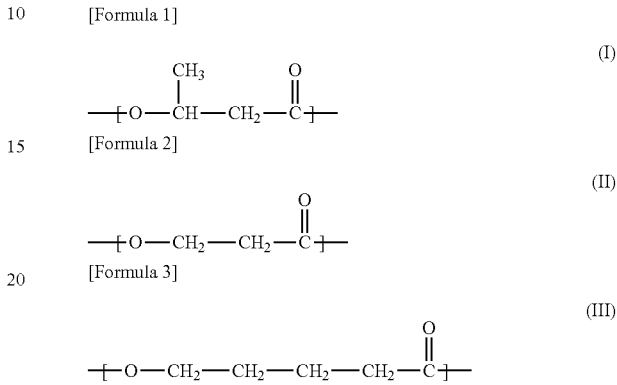

[Formula 2]

[Formula 3]

The 3HB unit represented by the formula (I) of the P(3HB-co-3HP-co-5HV) produced by the present method has asymmetric carbon at the three position, and all of its steric configurations are an (R)-configuration. In addition, an order (sequence) of the 3HB unit, the 3HP unit, and the 5 HV unit of the P(3HB-co-3HP-co-5HV) varies and includes all sequences of 3HB-3HB, 3HP-3HP, 5HV-5HV, 3HB-3HP, 3HB-5HV, 3HP-5HV, 3HP-3HB, 5HV-3HB, and 5HV-3HP. Furthermore, a percentage of the 5HV unit of the P(3HB-co-3HP-co-5HV) produced by the present method may be, for example, 10 to 35 mol %, and preferably 10 to 20 mol %.

Examples of the weight average molecular weight ($M_w$) of the P(3HB-co-3HP-co-5HV) produced by the present method include $40 \times 10^3$ to $170 \times 10^3$. Examples of the number average molecular weight ($M_n$) of the P(3HB-co-3HP-co-5HV) produced by the present method include $10 \times 10^3$ to $75 \times 10^3$. Examples of the polydispersity ($M_w/M_n$) of the P(3HB-co-3HP-co-5HV) produced by the present method include 1.5 to 3.5.

According to the mechanical characteristics of the PHA including 5HV units of the P(3HB-co-3HP-co-5HV) produced by the present method, the PHA produced by the present method is more flexible as compared with a conventional PHA, and forms a highly transparent film.

The PHA including 5HV units of the P(3HB-co-3HP-co-5HV) produced by the present method has degradable properties by lipases. The degradable properties by lipases of the PHA including 5HV units produced by the present method can be evaluated, for example, by incubating a film formed of the PHA including 5HV units together with a lipase and evaluating erosion of the film. In the case of significant erosion (that is, weight loss of the film) as compared with a film formed of a poly(3HB) homopolymer (P(3HB)) or a poly(3HP) homopolymer (P(3HP)) which has no degradable properties by lipases, it can be determined that the PHA including 5HV units has a good degradable property by the lipase.

Furthermore, the PHA including 5HV units of the P(3HB-co-3HP-co-5HV) produced by the present method has low toxicity to cells. The cell toxicity of the PHA including 5HV units produced by the present method can be evaluated, for example, by culturing cells in a plate coated with the PHA including 5HV units and evaluating the cellular viability. If there is no significant difference as compared with the cellular viability on a typical cell culture plate, it can be determined that the PHA including 5HV units has low or almost no toxicity to cells.

Examples

Hereinafter, the present invention will be described in more detail with reference to Examples. However, the technical scope of the present invention is not limited to thereto.

1. MATERIALS AND METHOD

<Bacterial Strain and Plasmid>

Ralstonia eutropha (or R. eutropha) H16 (ATCC 17699, wild type) or Ralstonia eutropha PHB-4 (DSM541) was used to produce PHAs.

Expression vectors pBBRMCS2$C_{Re}$, pBBR1KmEX22 (Taguchi, S.; Matsusaki, H.; Matsumoto, K.; Takase, K.; Taguchi, K.; Doi, Y., Polymer International 2002, 51, 899-906.), and pBBREE32d13 (Tsuge, T.; Saito, Y.; Kikkawa, Y.; Hiraishi, T.; Doi, Y., Macromolecular Bioscience 2004, 4, 238-242.) respectively had a PHA synthase gene (Pha$C_{Re}$; nucleotide sequence: SEQ ID NO: 1, amino acid sequence: SEQ ID NO: 2) derived from Ralstonia eutropha, a PHA synthase 1 gene (PhaC1$_{Ps}$; nucleotide sequence: SEQ ID NO: 3, amino acid sequence: SEQ ID NO: 4) derived from Pseudomonas sp. 61-3, and a PHA synthase gene (Pha$C_{Ac}$; nucleotide sequence: SEQ ID NO: 5, amino acid sequence: SEQ ID NO: 6) derived from Aeromonas caviae. Each of the PHA synthase genes was positioned between its own natural promoter and a terminator derived from Ralstonia eutropha. These plasmids (expression vectors) were used to express PHA synthases in Ralstonia eutropha PHB-4.

The expression vector pBBRMCS2$C_{Re}$ was constructed by self-ligation of blunt end DNA fragments obtained by digesting pBBRMCS2CAB$_{Re}$ (Taguchi, S.; Maehara, A.; Takase, K.; Nakahara, M.; Nakamura, H.; Doi, Y., Ferns Microbiology Letters 2001, 198, 65-71.) with Sse 83871 and Nde I.

<Culture Condition>

First, Ralstonia eutropha H16 or Ralstonia eutropha PHB-4 to which a PHA synthase gene was introduced was cultured in a 500 mL flask including 100 mL of a rich culture medium containing 1.0 g of meat extract, 1.0 g of polypeptone, and 0.2 g of yeast extract at 30° C. for 14 hours. After culturing, the cells were centrifuged at 5000 rpm for 15 minutes. Under these culture conditions, accumulation of polymers in the cells was not observed.

Then, in order to promote polymer synthesis, the collected cells were re-suspended in an inorganic culture medium (100 mL) that contained various carbon substrates as only carbon source but did not contain nutrients. The inorganic culture medium contained 2.8 g of $KH_2PO_4$, 3.32 g of $Na_2HPO_4$, 0.25 g of $MgSO_2.7H_2O$, and 1 mL of a minor element solution with respect to 1 L of distilled water. The minor element solution contained 20 g of $FeCl_3.6H_2O$, 10 g of $CaCl_2.H_2O$, 0.03 g of $CuSO_4.6H_2O$, 0.05 g of $MnCl_2.4H_2O$, and 0.1 g of $ZnSO_4.7H_2O$ (with respect to 1 L of 0.5N HCl).

The re-suspended cells were incubated in a culture medium (pH 7.0) which did not contain nitrogen at 30° C. for a predetermined time, and after the incubation, the cells were collected through centrifugation and then lyophilized.

<Extraction of Polymer from Cell>

After the collected cells were lyophilized as such, a polymer was extracted using chloroform in a glass tube having a screw cap at 60° C. for 2 days. The extract was filtered through a filter paper, thereby removing cellular debris.

Then, 10 times amount of methanol was added to the extract, and the polymer was precipitated. The precipitate was collected on a filter paper and then dried, and a weight of the polymer was measured. The content of the polymer was calculated on the basis of dry cell weight (DCW). In addition, the obtained polymer was provided for additional assay to be described below.

<Assay of Polymer>

The composition and the sequence distribution of the obtained copolymer described above were determined by $^1$H-NMR spectrum and $^{13}$C-NMR spectrum (Bruker-500 spectrometer). The 400 MHz $^1$H-NMR spectrum was recorded at a pulse width of 5 ms, 32000 data points, and 16 integration with respect to a $CDCl_3$ solution (10 mg/mL) of the PHA at 27° C. The 100 MHz $^{13}$C-NMR spectrum was recorded at a pulse width of 5 ms (pulse angle of 45°), a pulse repetition period of 0.7 s, a spectrum width of 23000 Hz, 32000 data points, and 8000 to 20000 integration with respect to a $CDCl_3$ solution (20 mg/mL) of the PHA at 27° C. Tetramethylsilane ($Me_4Si$) was used as an internal chemical shift standard.

The molecular weight of the polymer was determined by using a Shimadzu 6A gel permeation chromatography (GPC) system including a Shodex 80M column at 40° C. Chloroform was used as an eluent at a flow velocity of 0.8 mL/min. The sample concentration was 5.0 mg/mL. The molecular weight was evaluated by using a polystyrene standard material.

Furthermore, differential scanning calorimetry (DSC) data was recorded with Perkin-Elmer DSC 8500 equipment including a cooling accessory at a temperature in the range of −90 to 210° C. at a nitrogen flow velocity of 20 mL/min. A melt crystallized film (10 mg) was enclosed in an aluminum plate and heated from −50° C. to 210° C. at a rate of 20° C./min. The melting temperature ($T_m$) was determined at the position of an endothermic peak.

With respect to the mechanical characteristics of the polymer, a stress-strain test of a solution cast film (10×2× 0.15 mm$^3$) manufactured with each polymer was carried out by using a small bench tester EZ test (manufactured by Shimazu Co., Ltd.) at room temperature at a strain rate of 10 mm/min.

<Enzymatic Degradation>

Enzymatic degradation of the PHA film was carried out in a 0.1 M phosphate buffer (pH 7.4) at 37° C. The PHA film (initial weight of about 4 mg; initial size of 10×10 mm; initial thickness of 0.05 mm) was placed in a test tube including a screw cap and containing 1.0 mL of a buffer. The reaction was started by addition of a lipase (500 μg, derived from porcine pancreas and produced by Wako Chemical LTD). The reaction solution was incubated in a shake flask at 37° C.

The film was regularly taken out and washed with water and vacuum-dried, so that the film reached a certain weight before assay. The molecular weight of an eroded PHA film was not different from that of a non-eroded PHA film. This suggests that the PHA was eroded from a surface of the film by the lipase.

<Cell Culture and In Vitro Cellular Viability>

Human mesenchymal stem cells (hMSC) were purchased from Lonza Walkersville Inc. (Walkerville, Md.) and then cultured in a growth medium containing Dulbecco's modification of Eagle's medium (DMEM) supplemented with 10% fetal bovine serum (FBS), 0.1 mM non-essential amino acid, and 1 ng/mL of a basic fibroblast growth factor (bFGF) in the presence of 100 U/mL of penicillin, 100 μg/mL of streptomycin, and 0.25 μg/mL of fungizone, within a 5% $CO_2$ incubator at 37° C.

The PHA was dissolved in chloroform at a final concentration of 10 wt %. 20 μL of the solution was placed in a 96-well plate. After a film forming process, the sample was vacuum-dried at room temperature for 2 weeks, and a small amount of chloroform was removed, and then sterilized with 100% ethanol and UV before further use.

Regarding the cellular viability assay, the hMSC (8000 cells/well) was seeded in the 96-well plate coated with the PHA film and cultured in a culture medium (100 μL) for 48 hours. After the culture, cell viability of the hMSC on the PHA film was evaluated by standard 3-(4,5-dimethylthiazol-2-yl)-5-(3-carboxymethoxyphenyl)-2-(4-sulfophenyl)-2H-tetrazolium (MTS) assay (Promega, Madison, Wis.) according to the manufacturer's instructions (n=3).

(5HV-CoA) were considered as only carbon source in the culture medium for producing polymer (Table 1).

TABLE 1

PHA biosynthesis from various long chain length lactones by Ralstonia eutropha H16[a]

| Carbon source (20 g/L) | DCW (mg) | Polymer content (wt %) |
|---|---|---|
| γ-valerolaetone | 164 | n.d.[b] |
| ε-caprolactone | 168 | n.d. |
| oxacyclododecane-2-one | 55 | n.d. |

[a]Cells were cultured in an MS culture medium containing carbon source (20 g/L) at 30° C. for 48 hours.
[b]n.d.: Not detected by $^1$H NMR assay.

In the case of using 20 g/L of sodium 5-hydroxyvalerate (5HVNa) and ω-pentadecalactone (ω-PDL) as carbon source, Ralstonia eutropha H16 produced a polymer including 5 mol % of 3HP and 1 mol % of 5HV, and a polymer including 2 mol % of 3HP and 1 mol % of 5HV, respectively (Table 2).

TABLE 2

PHA biosynthesis from sodium 5-hydroxyvalerate and ω-pentadecalactone by Ralstonia eutropha H16 or Ralstonia eutropha PHB-4 including various PHA synthase genes[a]

| Sample No. | Strain | PHA synthase | Carbon source (g/L) | DCW (mg) | Polymer content (wt %) | Monomer composition[b] (mol %) | | |
|---|---|---|---|---|---|---|---|---|
| | | | | | | 3HB | 3HP | 5HV |
| | | | 5HVNa | | | | | |
| 1 | H16 | | 20 | 603 ± 50 | 34 ± 7 | 94 | 5 | 1 |
| | | | ω-PDL | | | | | |
| 2 | H16 | | 20 | 571 ± 160 | 17 ± 9 | 97 | 2 | 1 |
| | | | 5HVNa | | | | | |
| 3 | PHB-4 | PhaC$_{Re}$ | 20 | 414 ± 18 | 42 ± 14 | 76 | 18 | 6 |
| 4 | PHB-4 | PhaC1$_{Ps}$ | 20 | 246 ± 7 | 8 ± 3 | 100 | | |
| 5 | PHB-4 | PhaC$_{Ac}$ | 20 | 274 ± 11 | 15 ± 4 | 90 | 7 | 3 |
| | | | ω-PDL | | | | | |
| 6 | PHB-4 | PhaC$_{Re}$ | 20 | 287 ± 54 | 10 ± 3 | 87 | 5 | 8 |
| 7 | PHB-4 | PhaC1$_{Ps}$ | 20 | 325 ± 9 | 25 ± 5 | 96 | 2 | 5 |
| 8 | PHB-4 | PhaC$_{Ac}$ | 20 | 228 ± 7 | 13 ± 1 | 88 | 5 | 7 |

[a]Cells including pBBRMCS2C$_{Re}$, pBBR1KmEX22, or pBBREE32d13 were cultured in an MS culture medium containing 5HVNa or ω-PDL (20 g/L) as only carbon source at 30° C. for 48 hours. H16: Ralstonia eutropha H16; PHB-4: Ralstonia eutropha PHB-4; PhaC$_{Re}$: PHA synthase derived from Ralstonia eutropha; PhaC1$_{Ps}$: PHA synthase 1 derived from Pseudomonas sp. 61-3; PhaC$_{Ac}$: PHA synthase derived from Aeromonas caviae.
[b]Monomer compositions were determined by $^1$H-NMR assay.
3HP: 3-hydroxypropionate;
3HB: 3-hydroxybutyrate;
5HV: 5-hydroxyvalerate.

The cellular viability was calculated by the following equation:

[Cellular viability %]=[Absorbance of a cell culture incubated on the PHA film at 490 nm]/[Absorbance of a cell culture incubated on the 96-well cell culture plate at 490 nm (positive control)]×100

2. RESULT AND DISCUSSION

Production of Polymer Including 5HV Unit by Microorganism

Sodium α-hydroxy alkanoate and lactones with various long chain lengths expected as precursors of 5HV monomer This result indicates that the 5HV-CoA can be supplied from the 5HVNa and the co-PDL through metabolism in Ralstonia eutropha. However, fractionation of 5HV in the polymer was very low. Therefore, although concentrations of 5HVNa and co-PDL in the culture medium were increased (20, 30, and 50 g/L), fractionation of 5HV in the polymer was not changed. This result indicates that the amount of 5HV-CoA is not increased in the cells, and/or substrate specificity of the PHA synthase to 5HV-CoA is low.

Therefore, at first the focus was on the substrate specificity of the PHA synthase. There was a review of production of PHA using Ralstonia eutropha PHB-4 (PHA-negative mutant) to which three kinds of PHA synthases (PHA synthase (PhaC$_{Re}$) derived from Ralstonia eutropha, PHA synthase (PhaC1$_{Ps}$) derived from *Pseudomonas* sp. 61-3, and PHA synthase (PhaC$_{Ac}$) derived from *Aeromonas caviae* having different substrate specificities were introduced, respectively.

A recombinant *Ralstonia eutropha* PHB-4 including a phaC$_{Re}$ gene produced a copolymer including the most amount of 3HP units (18 mol % and 5 mol %) and 5HV units (6 mol % and 8 mol %) in the presence of 20 g/L of 5HVNa and the ω-PDL (Table 2). It is known that PhaC$_{Re}$ can produce P(3HB-co-4HB) having various monomer compositions. The present result indicates that PhaC$_{Re}$ can recognize not only 4HB, but also 5HV, and the PhaC$_{Re}$ has a wide range of substrate specificity to various main chain length monomers (Saito, Y.; Doi, Y., International Journal of Biological Macromolecules 1994, 16, 99-104.). As such, the PhaC$_{Re}$ is a good lead enzyme for manufacturing a mutant highly capable of incorporating 5HV-CoA.

In addition, when the recombinant *Ralstonia eutropha* PHB-4 including the phaC$_{Re}$ gene was cultured, a concentration of the carbon source in the MS culture medium was changed in the range of 10 to 100 g/L as listed in Table 3.

*Ralstonia eutropha* (FIG. 1). In addition, acetyl-CoA (C2) is formed incidentally in each β oxidation cycle, and then, 3HB-CoA is synthesized by a β-ketothiolase and an NADPH-dependent acetoacetyl-CoA reductase from acetyl-CoA. 3HB unit suggests that the β oxidation pathway as a main component of the polymer produced in the present example is active in *Ralstonia eutropha*. Therefore, due to inhibition of the oxidation pathway, a content of 5HV units may be increased in a subsequent step.

<NMR Assay of Produced Polymer>

Figure 2:
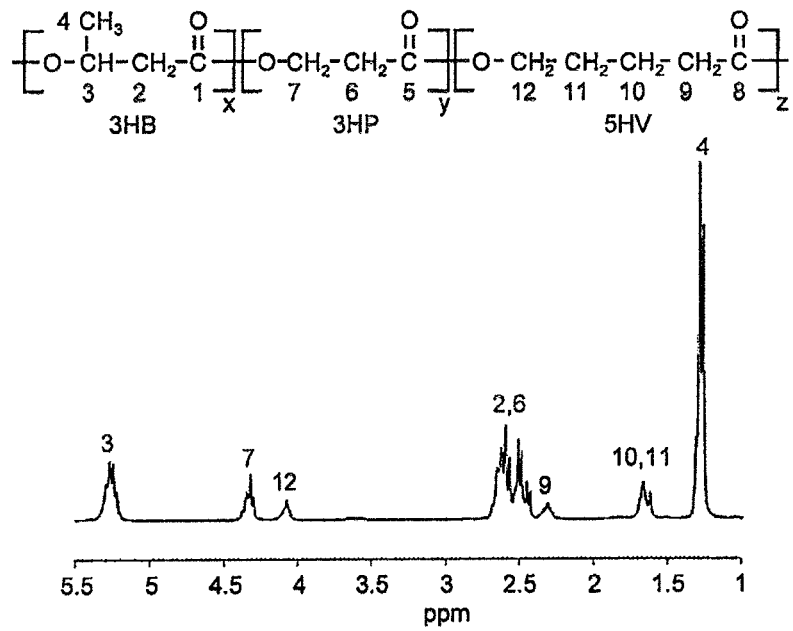
FIG. 2 illustrates NMR spectra of P(3HB-co-3HP-co-5HV) (Sample No. 10 in Table 3) produced in a recombinant Ralstonia eutropha PHB-4 having an expression vector pBBRMCS2C$_{Re}$. (A) $^1$H NMR, (B)$^{13}$C NMR.
Figure 2:
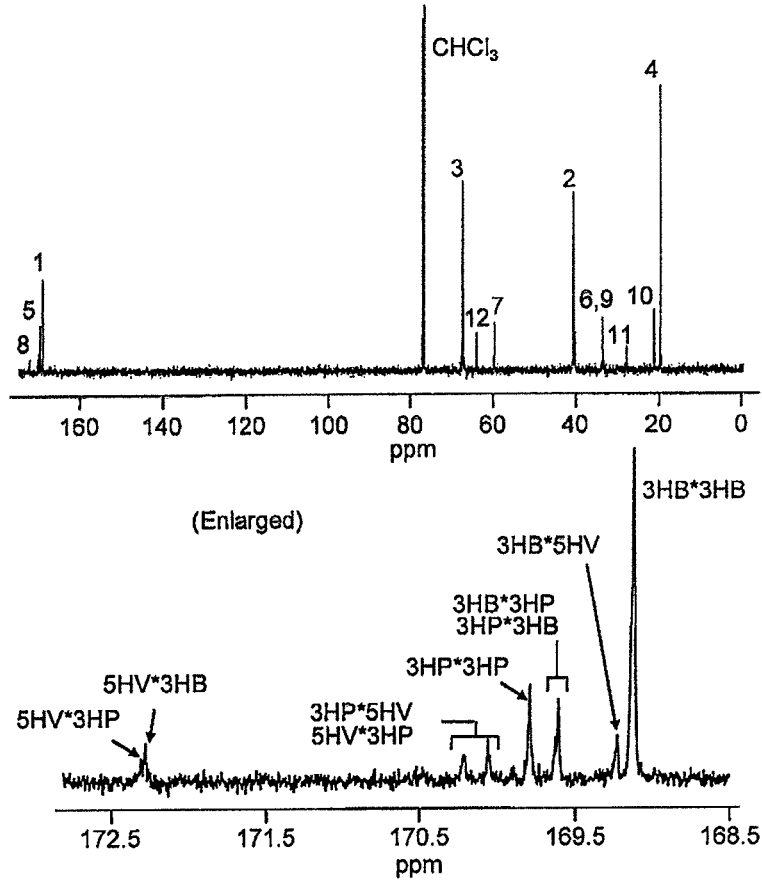

FIG. 2A illustrates a typical $^1$H-NMR spectrum of a polymer (Sample No. 10 in Table 3) in CDCl$_3$. According to this result, it becomes clear that the polymer has typical peaks of 3HB and 3HP units. The other peak was assigned to a peak from a 5HV unit of a P(3HB-co-3HV-co-5HV) copolymer (Doi, Y.; Tamaki, A.; Kunioka, M.; Soga, K., Makromol. Chem., Rapid Commun 1987, 8, 631-635.).

$^{13}$C-NMR assay of Sample No. 10 in Table 3 exhibits typical peaks of 3HB, 3HP, and 5HV units (FIG. 2B). A carbonyl resonance of 168.5 to 172.5 ppm exhibits complicated peaks occurring at various dyad sequences including

TABLE 3

PHA biosynthesis from sodium 5-hydroxyvalerate and ω-pentadecalactone by *Ralstonia eutropha* PHB-4 including PHA synthase gene derived from *Ralstonia eutropha*[a]

| Sample No. | Carbon source (g/L) | DCW (mg) | Polymer content (wt %) | Monomer composition (mol %)[b] 3HB | 3HP | 5HV | Molecular weight[c] M$_w$ (×10$^3$) | M$_n$ (×10$^3$) | M$_w$/M$_n$ |
|---|---|---|---|---|---|---|---|---|---|
| 5HVNa | | | | | | | | | |
| 9 | 10 | 470 ± 15 | 26 ± 4 | 76 | 18 | 6 | 89 | 40 | 2.2 |
| 10 | 20 | 414-18 | 42 ± 14 | 77 | 18 | 5 | 76 | 36 | 2.1 |
| 11 | 30 | 260 ± 8 | 15 ± 2 | 71 | 23 | 6 | 63 | 27 | 2.3 |
| 12 | 50 | 247 ± 5 | Small amount | 51 | 17 | 32 | 41 | 12 | 3.4 |
| | 80 | Small amount | n.d. | | | | | | |
| ω-PDL | | | | | | | | | |
| 13 | 10 | 257 ± 26 | 10 ± 3 | 86 | 4 | 9 | 168 | 72 | 2.3 |
| 14 | 20 | 287 ± 54 | 10 ± 3 | 85 | 5 | 10 | 139 | 53 | 2.6 |
| 15 | 30 | 244 ± 58 | 12 ± 0 | 85 | 5 | 10 | 140 | 53 | 2.6 |
| 16 | 50 | 316 ± 8 | 13 ± 5 | 84 | 5 | 11 | 142 | 55 | 2.6 |
| 17 | 80 | 220 ± 33 | 6 ± 3 | 84 | 5 | 11 | 116 | 41 | 2.9 |
| | 100 | Small amount | n.d. | | | | | | |

[a]Cells including pBBRMCS2C$_{Re}$ were cultured in an MS culture medium containing 5HVNa or ω-PDL as only carbon source at various concentrations at 30° C. for 48 hours.
[b]Monomer compositions were determined by $^1$H-NMR assay.
3HP: 3-hydroxypropionate;
3HB: 3-hydroxybutyrate;
5HV: 5-hydroxyvalerate.
[c]M$_w$: weight average molecular weight; M$_n$: number average molecular weight; M$_w$/M$_n$: polydispersity.

In the case of using 5HVNa at a concentration of 10 to 50 g/L as carbon source, 5HV in the polymer was increased together with 5HVNa in a culture medium (5 to 32 mol %). However, there was no significant change in concentration of ω-PDL and monomer composition. It was difficult to dissolve ω-PDL in the culture medium. It is deemed that the reason why a PHA composition was not changed by ω-PDL at various concentrations was low dissolubility of ω-PDL.

The produced polymer includes monomer units having odd-numbered carbon atoms such as 3HP (C3) units and 5HV (C5) units. These results incicate that an acyl-CoA unit is shortened by 2 carbon atoms in each β oxidation cycle, and thus, 3HP and 5HV-CoA are mainly supplied from 5HVNa (C5) and ω-PDL (C15) through β oxidation cycle in 3HB, 3HP, and 5HV units. The peaks at 169.1 ppm, 169.8 ppm, and 169.6 ppm are identical with carbonyl resonances from sequences of 3HB*3HB, 3HP*3HP and 3HB*3HP/3HP*3HB, and are already observed from the P(3HB-co-3HP) copolymer (Nakamura, S.; Kunioka, M.; Doi, Y., Journal of Macromolecular Science-Chemistry 1991, A28, 15-24.). The other peaks appear at 169.2 ppm, 170.0 ppm, 170.2 ppm, and 172.3 ppm, which indicates that 3HB and 3HP units are combined with a 5HV unit. The peak at 169.2 ppm is increased when a polymer (Sample No. 14 in Table 3) including 5 mol % 3HP and 10 mol % 5HV is measured, and thus, it is identified as a sequence of 3HB*5HV/5HV*3HB. Then, it is assumed that the peaks at 170.0 ppm and 170.2 ppm is derived from a sequence of 3HP*5HV/

5HV*3HP. Finally, a peak was divided from a carbon including 5HV units (172.3 ppm). In a copolymer including a 5HV unit of low molar fraction, a large amount of dyad sequences 5HV*3HB may exist. Therefore, a main peak from the 5HV unit is assigned to a sequence of 5HV*3HB. In addition, since 3HP is a secondary component of the copolymer, it is assumed that a small peak is a sequence of 5HV*3HP.

$^{13}$C-NMR assay clearly exhibits peaks of dyad sequences of 5HV*3HB/3HB*5HV and 5HV*3HP/3HP*5HV in the copolymer. Therefore, it is first confirmed in the present application that PhaC$_{Re}$ constitutively has an ability of sequentially polymerizing 5HV-CoA.

<Molecular Weight and Heat Characteristic of P(3HB-co-3HP-co-5HV) Copolymer>

Molecular weights of the produced P(3HB-co-3HP-co-5HV) are summarized in Table 3 above. As the fractions of 3HP and 5HV increased, a molecular weight of the polymer tended to decrease (41000 to 168000). This result suggests that a molecular weight decreases due to injection of 3HP and 5HV units to a polymer chain.

Figure 3:
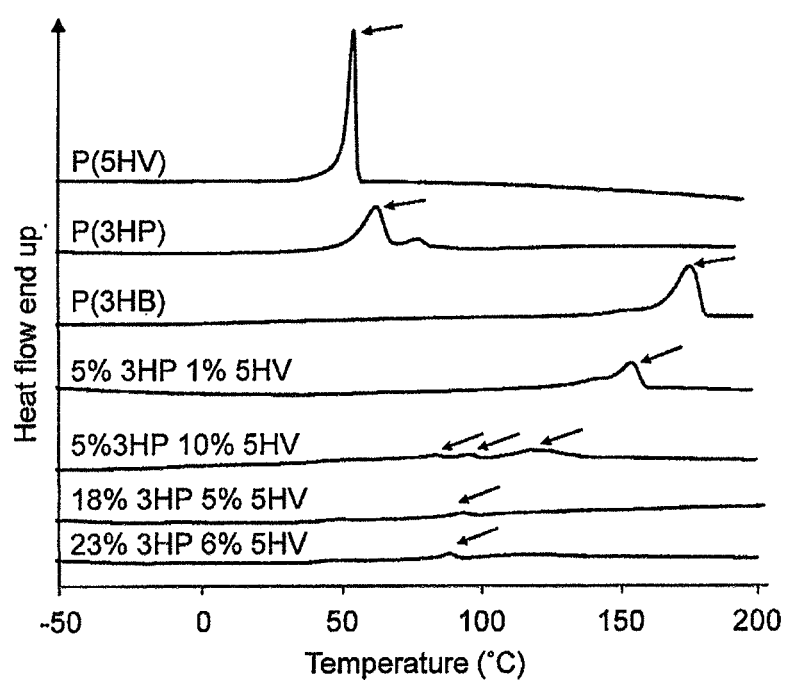
FIG. 3 illustrates a result of DSC analysis on P(3HB), P(3HP), P(5HV), and P(3HB-co-3HP-co-5HV). P(3HB-co-3HP-co-5HV) of 5% 3HP 1% 5HV: P(3HB-co-5 mol % 3HP-co-1 mol % 5HV), 5% 3HP 10% 5HV: P(3HB-co-5 mol % 3HP-co-10 mol % 5HV), 18% 3HP 5% 5HV: P(3HB-co-18 mol % 3HP-co-5 mol % 5HV), and 23% 3HP 6% 5HV: P(3HB-co-23 mol % 3HP-co-6 mol % 5HV) are expressed by Sample Nos. 1, 14, 10, and 11, respectively, listed in Tables 2 and 3. P(3HB) is produced by Ralstonia eutropha H16 from fructose. P(3HP) and P(5HV) are chemically synthesized (Abe, H.; Doi, Y.; Aoki, H.; Akehata, T.; Hori, Y.; Yamaguchi, A., Macromolecules 1995, 28, 7630-7637.). The arrows indicate peaks of melting temperatures ($T_m$).

FIG. 3 illustrates the DSC trace of P(3HB), P(3HP), P(5HV) and P(3HB-co-3HP-co-5HV). Melting temperatures ($T_m$) of P(3HB), P(3HP), and P(5HV) homopolymers were 173° C., 67° C., and 55° C., respectively. The $T_n$ value of a P(3HB-co-3HP-co-5HV) copolymer was decreased together with contents of 3HP and 5HV units as compared with the P(3HB) homopolymer. In addition, when the produced P(3HB-co-5 mol % 3HP-co-10 mol % 5HV) was measured, three small peaks were detected. These results indicate that the copolymer has various compositions and is formed of some crystallites.

Enthalpy of a melting value ($\Delta H_m$) of the P(3HB-co-3HP-co-5HV) was lower than that of the homopolymer, and for example, melting values ($\Delta H_m$) of P(94 mol % 3HB-co-5 mol % 3HP-co-1 mol % 5HV) and P(85 mol % 3HB-co-5 mol % 3HP-co-10 mol % 5llV) were 43 J/g and 2 J/g, respectively. Meanwhile, melting values ($\Delta H_m$) of P(3HB) and P(3HP) were 70 J/g and 60 J/g, respectively. This suggests that crystallinity of the copolymer was decreased together with the fractions of 3HP and 5HV. These results indicate that crystallization of a P(3HB-co-3HP-co-5HV) copolymer is inhibited by copolymerization of 3HB, 3HP, and 5HV units.

<Mechanical Characteristic of P(3HB-co-3HP-co-5HV) Copolymer>

A test result of the mechanical characteristics of each P(3HB-co-3HP-co-5HV) copolymer is listed in Table 4. Each value of mechanical characteristic data in Table 4 is the mean value and the standard deviation of three measurement values.

TABLE 4

Mechanical characteristics of P(3HB-co-3HP-co-5HV) having various monomer compositions

| Polymer | Young's modulus (MPa) | Tensile strength (MPa) | Breaking extensibility (%) |
|---|---|---|---|
| P(3HB-co-18 mol % 3HP-co-5 mol % 5HV) | 1600 ± 170 | 29 ± 13 | 37 ± 17 |
| P(3HB-co-5 mol % 3HP-co-10 mol % 5HV) | 970 ± 290 | 12 ± 7 | 37 ± 4 |
| P(3HB-co-9 mol % 3HP-co-14 mol % 5HV) | 1400 ± 170 | 14 ± 7 | 15 ± 3 |

In Table 4, P(3HB-co-18 mol % 3HP-co-5 mol % 5HV) and P(3HB-co-5 mol % 3HP-co-10 mol % 5HV) corresponded to Sample Nos. 10 and 14, respectively, listed in Table 3. P(3HB-co-9 mol % 3HP-co-14 mol % 5HV) corresponded to Sample No. 30 or 31 listed in Table 6.

As listed in Table 4, the P(3HB-co-3HP-co-5HV) exhibited a flexible property along with an increase in composition of 5HV and 3HP. As for mechanical characteristics as a film, P(3HB-co-18 mol % 3HP-co-5 mol % 5HV) was a material that had relatively strong and also flexible.

<In Vitro Enzymatic Degradation of P(3HB-co-3HP-co-5HV) Film>

Figure 4:
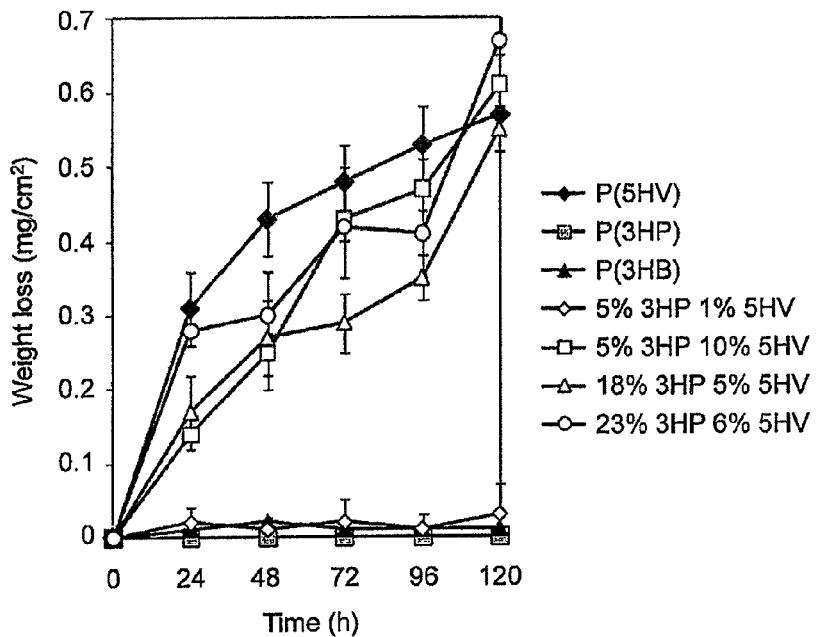
FIG. 4 illustrates enzymatic degradation profiles of PHA films (initial weight: about 4 mg) in an aqueous solution of porcine pancreatic-derived lipase under 37° C. and pH 7.4. The error bars represent standard deviations of samples (n=2).
Figure 4:
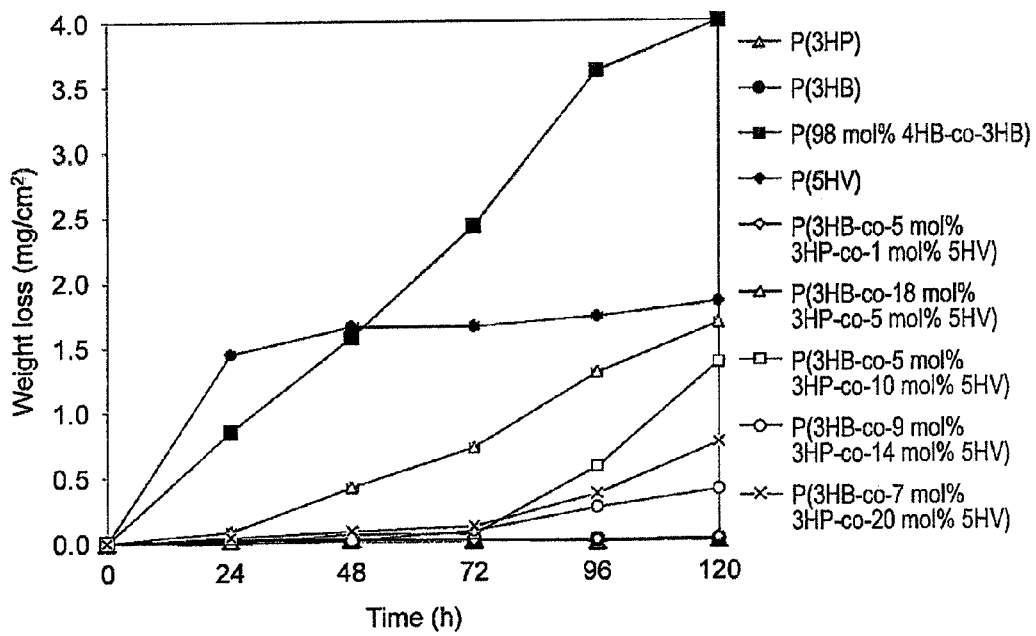

FIG. 4 illustrates a weight loss profile of P(3HB), P(3HP), P(5HV), and P(3HB-co-3HP-co-5HV) films using a porcine pancreatic-derived lipase.

As illustrated in FIG. 4(A), it was interesting that P(3HB), P(3HP), and P(3HB-co-5 mol %3HP-co-1 mol % 5HV) were not eroded by the lipase, whereas P(5HV), P(3HB-co-5 mol % 3HP-co-10 mol % 5HV), P(3HB-co-18 mol % 3HP-co-5 mol % 5HV), and P(3HB-co-23 mol % 3HP-co-6 mol % 5HV) were eroded. In addition, an erosion rate of the P(3HB-co-3HP-co-5HV) film was substantially the same as that of the P(5HV) film.

As illustrated in FIG. 4(B), P(98 mol % 4HB-co-3HB) and P(5HV) known for degradable properties by lipases exhibited an excellent degradable property. Also, P(3HB-co-5 mol % 3HP-co-10 mol % 5HV) synthesized in the present research exhibited an excellent degradable property. The other copolymer including 5HV exhibited degradable properties by lipases but had properties different from those of P(3HB) and P(3HP).

These results indicate that a 5HV unit is digested by a lipase, and the 5HV unit is a promising monomer for improving degradable properties by lipases of a P(3HB-co-3HP) copolymer.

Although PHAs including various side chain length units are efficiently digested by PHA depolymerases, most of them except PHAs including 4HB units cannot be digested by lipases. Therefore, P(3HB-co-3HP-co-5HV) is a new PHA type sensitive to degradation by an intracellular lipase. An in vivo biodegradable property of P(3HB-co-3HP-co-5HV) is expected to be relatively increased as compared with P(3HB), P(3HP), and P(5HV).

<Cellular Proliferation on P(3HB-co-3HP-co-5HV) Film>

Figure 5:
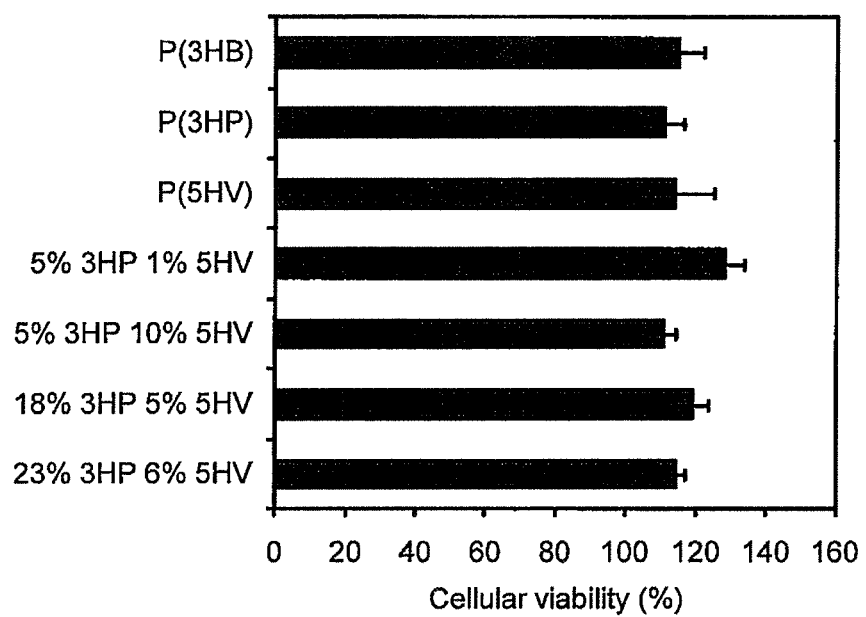
FIG. 5 illustrates the cellular viability of hMSC seeded onto PHA films determined by absorbance at 490 nm measured by using a cell culture after 48-hours incubation. The 100% cellular viability is calculated from a positive control (a cell culture after being seeded onto a cell culture plate and incubated for 48 hours). The error bars represent standard deviations of samples (n=3). P(3HB-co-3HP-co-5HV) of 5% 3HP 1% 5HV: P(3HB-co-5 mol % 3HP-co-1 mol % 5HV), 5% 3HP 10% 5HV: P(3HB-co-5 mol % 3HP-co-10 mol % 5HV), 18% 3HP 5% 5HV: P(3HB-co-18 mol % 3HP-co-5 mol % 5HV), and 23% 3HP 6% 5HV: P(3HB-co-23 mol % 3HP-co-6 mol % 5HV) are expressed by Sample Nos. 1, 14, 10, and 11, respectively, listed in Tables 2 and 3. P(3HB) is produced by Ralstonia eutropha H16 from fructose. P(3HP) and P(5HV) are chemically synthesized (Abe, H.; Doi, Y.; Aoki, H.; Akehata, T.; Hori, Y.; Yamaguchi, A., Macromolecules 1995, 28, 7630-7637.).

The cellular viability of the hMSC on the PHA film was evaluated by using MTS assay (FIG. 5). A 100% cellular viability was calculated from a cell culture seeded on a cell culture plate (after 48-hours incubation) as a positive control. The cellular viability of the hMSC was substantially the same in the case of using P(3HB), P(3HP), P(5HV), and P(3HB-co-3HP-co-5HV) films (about 110%). In the case of using a P(3HB-co-5 mol % 3HP-co-1 mol % 5HV) film, the cellular viability of the hMSC was slightly increased (127%) as compared with the other films. These results indicate that the produced P(3HB-co-3HP-co-5HV) has a biocompatible property equivalent to or higher than a biocompatible property of P(3HB) which is sufficient for medical use.

<PHA Biosynthesis from ω-PDL by *Ralstonia eutropha* PHB-4 Including Mutant of PHA Synthase (PhaC$_{Re}$) Derived from *Ralstonia eutropha*>

Results of PHA biosynthesis from ω-PDL by *Ralstonia eutropha* PHB-4 including a mutant of a PHA synthase (PhaC$_{Re}$) derived from *Ralstonia eutropha* are listed in Tables 5 and 6. Tables 5 and 6 exhibit results of the same experiment.

In Tables 5 and 6, each PhaC$_{Re}$ mutant is as follows:

M-22(V470M): Mutant including substitution from valine to methionine at a position of 470 of an amino acid in a wild type (amino acid sequence: SEQ ID NO: 2);

E-11/S12-1(F420S): Mutant including substitution from phenylalanine to serine at a position of 420 of an amino acid in a wild type (amino acid sequence: SEQ ID NO: 2);

2-12(L358P): Mutant including substitution from leucine to proline at a position of 358 of an amino acid in a wild type (amino acid sequence: SEQ ID NO: 2);

1-14(S174P): Mutant including substitution from serine to proline at a position of 174 of an amino acid in a wild type (amino acid sequence: SEQ ID NO: 2);

E-11/S12(S80P/F420S): Mutant including substitution from serine to proline at a position of 80 of an amino acid and substitution from phenylalanine to serine at a position of 420 of an amino acid in a wild type (amino acid sequence: SEQ ID NO: 2);

B-1(N519S): Mutant including substitution from asparagine to serine at a position of 519 of an amino acid in a wild type (amino acid sequence: SEQ ID NO: 2);

E-11(S80P): Mutant including substitution from serine to proline at a position of 80 of an amino acid in a wild type (amino acid sequence: SEQ ID NO: 2);

B-7(S35P): Mutant including substitution from serine to proline at a position of 35 of an amino acid in a wild type (amino acid sequence: SEQ ID NO: 2); and 1-11(N426S): Mutant including substitution from asparagine to serine at a position of 426 of an amino acid in a wild type (amino acid sequence: SEQ ID NO: 2).

TABLE 5

PHA biosynthesis from ω-PDL by *Ralstonia eutropha* PHB-4 including mutant of PHA synthase derived from *Ralstonia eutropha*

| Sample No. | Carbon source (g/100 mL) | PhaC$_{Re}$ mutant | Dry cell weight (mg) | Polymer content (wt %) | Monomer composition (mol %) | | |
|---|---|---|---|---|---|---|---|
| | | | | | 3HB | 3HP | 5HV |
| 18 | ω-PDL 2 g | Wild type | 287 ± 54 | 10 ± 3 | 85 | 5 | 10 |
| 19 | | M-22 (V470M)[2] | 297 | 11 | 71 | 9 | 21 |
| 20 | | E-11/S12-1 (F420S)[1] | 274 | 7 | 76 | 7 | 16 |
| 21 | | 2-12 (L358P)[2] | 477 | 26 | 76 | 8 | 16 |
| 22 | | 1-14 (S174P)[2] | 224 | 5 | 73 | 7 | 20 |
| 23 | | E-11/S12(S80P/F420S)[1] | 245 | 7 | 76 | 8 | 16 |
| 24 | | B-1 (N519S)[2] | 242 | 3 | 71 | 8 | 21 |
| 25 | | E-11 (S80P)[2] | 237 | 7 | | NT | |
| 26 | | B-7 (S35P)[2] | 315 | 11 ± 5 | 78 | 9 | 13 |
| 27 | | 1-11 (N426S)[2] | 235 | 4 ± 1 | 71 | 7 | 22 |

NT: Not tested
References:
[1]In vitro evolution of a polyhydroxybutyrate synthase by intragenic suppression-type mutagenesis. Taguchi S, Nakamura H, Hiraishi T, Yamato I, Doi Y., J Biochem. (2002) 131, 801-806.
[2]Analysis of mutational effects of a polyhydroxybutyrate (PHB) polymerase on bacterial PHB accumulation using an in vivo assay system. Taguchi S, Maehara A, Takase K, Nakahara M, Nakamura H, Doi Y., FEMS Microbiol Lett. (2001) 198, 65-71.

TABLE 6

| Sample No. | PHA synthase | DCW (mg) | Polymer content (wt %) | Monomer composition (mol %)[a] | | | Molecular weight[b] | | |
|---|---|---|---|---|---|---|---|---|---|
| | | | | 3HB | 3HP | 5HV | Mw (×10$^3$) | Mn (×10$^3$) | M$_w$/M$_n$ |
| 28 | Wild type | 287 ± 74 | 12 ± 2 | 85 | 8 | 10 | 139 | 53 | 2.6 |
| 29 | 1-14 (S174P) | 216 ± 6 | 9 ± 5 | 73 | 7 | 20 | 117 | 80 | 1.5 |
| 30 | M-22 (V470M) | 357 ± 135 | 8 ± 2 | 77 | 9 | 14 | 82 | 50 | 1.7 |
| 31 | B-1 (N5198) | 259 ± 28 | 13 ± 10 | 77 | 9 | 14 | 114 | 73 | 1.6 |
| 32 | E-11 (S80P) | 264 ± 58 | 13 ± 12 | 78 | 8 | 14 | 143 | 82 | 1.7 |
| 33 | 1-11 (N426S) | 321 ± 107 | 22 ± 12 | 80 | 7 | 13 | 115 | 78 | 1.5 |
| 34 | 2-12 (L358P) | 317 ± 107 | 17 ± 9 | 82 | 8 | 10 | 128 | 80 | 1.6 |
| 35 | E-11/S12 (S80P/F420S) | 248 ± 6 | 22 ± 10 | 80 | 8 | 12 | 138 | 101 | 1.4 |
| 36 | E-11/S12-1 (F420S) | 336 ± 103 | 22 ± 10 | 82 | 8 | 10 | 115 | 72 | 1.6 |

3HP: 3-hydroxypropionate;
3HB: 3-hydroxybutyrate;
5HV: 5-hydroxyvalerate.
Cells including pBBRMCS2C$_{Re}$ were cultured in an MS culture medium containing 20 g/L of ω-PDL as only carbon source at 30° C. for 48 hours.
[a]Monomer compositions were determined by $^1$H-NMR assay.
[b]M$_w$: weight average molecular weight; M$_n$: number average molecular weight; M$_w$/M$_n$: polydispersity.

As listed in Tables 5 and 6, through PHA biosynthesis from ω-PDL by *Ralstonia eutropha* PHB-4 including a mutant of a PHA synthase (PhaC$_{Re}$) derived from *Ralstonia eutropha*, a PHA including 20% or more of 5HV units was successfully synthesized. In addition, although 5HV as a monomer unit is included, productivity (polymer content) is higher than it is at present.

3. CONCLUSION

The present example indicates that a novel PHA type including 3HP and 5HV units from 5HVNa or ω-PDL derived from a wild type or a recombinant *Ralstonia eutropha* was successfully produced. A composition of P(3HB-co-3HP-co-5HV) could be controlled by adjusting a concentration of carbon source in a culture medium.

The produced copolymer exhibited low toxicity to cells and high degradable properties by lipases. An increase in enzymatic degradable property of P(3HB-co-3HP-co-5HV) is likely to be caused by introduction of 5HV units into the copolymer and decrease in crystallinity thereof.

Furthermore, in the present example, enzymatic degradable properties and toxicity to cells of a PHA including 5HV units were studied first. Also, according to the present example, it is confirmed that a PHA having long main chain units can be usefully used as a biomaterial.

All the publications, patents, and patent applications cited in the present specification are incorporated herein by reference in their entirety.

---

The invention claimed is:

1. A polyhydroxyalkanoate copolymer consisting of a constituting unit represented by the following formula (I), a constituting unit represented by the following formula (II), and a constituting unit represented by the following formula (III):

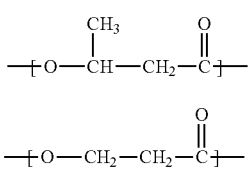

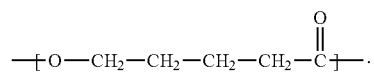

2. The polyhydroxyalkanoate copolymer according to claim 1, wherein the constituting unit represented by the formula (I) has asymmetric carbon at the three position, and all of its steric configurations are in (R)-configuration.

3. The polyhydroxyalkanoate copolymer according to claim 1, wherein a percentage of the constituting unit represented by the formula (III) in the copolymer is 10 to 35 mol %.

4. The polyhydroxyalkanoate copolymer according to claim 1, wherein the polydispersity ($M_w/M_n$) of the copolymer is 1.5 to 3.5.

* * * * *